United States Patent
Mulzer et al.

(10) Patent No.: US 6,605,726 B1
(45) Date of Patent: Aug. 12, 2003

(54) METHOD FOR PRODUCING EPOTHILONE B AND DERIVATIVES, AND INTERMEDIATE PRODUCTS FOR THIS METHOD

(75) Inventors: Johann Mulzer, Berlin (DE); Andreas Mantoulidis, Vienna (AT); Elisabeth Öhler, Klosterneuburg (AT)

(73) Assignee: Schering AG (DE)

( * ) Notice: Subject to any disclaimer, the term of this patent is extended or adjusted under 35 U.S.C. 154(b) by 0 days.

(21) Appl. No.: 09/807,370

(22) PCT Filed: Oct. 14, 1999

(86) PCT No.: PCT/EP99/07746
§ 371 (c)(1),
(2), (4) Date: Jun. 1, 2001

(87) PCT Pub. No.: WO00/23452
PCT Pub. Date: Apr. 27, 2000

(30) Foreign Application Priority Data

Oct. 14, 1998 (DE) .......................... 198 48 306

(51) Int. Cl.[7] .............................. C07D 493/04
(52) U.S. Cl. ..................................... 548/202
(58) Field of Search ........................ 548/202

(56) References Cited

FOREIGN PATENT DOCUMENTS

| WO | 9310121 | 5/1993 |
| WO | 9719086 | 5/1997 |
| WO | 9825929 | 6/1998 |

OTHER PUBLICATIONS

Claus E et al: "Synthesis of the C1–C9 Segment of Epothilons" Tetrahedron Letters,NL,Elsevier Science Publishers, Amsterdam, Bd. 38, Nr. 8, 24. (Feb. 24, 1997), Seiten 1359–1362, XP004053058 ISSN: 0040–403.

Mulzer J et al: "Easy Access to the Epothilone Family—Synthesis of Epothilone B" Tetrahedron Letters,NL, ELsevier Science Publishers, Amsterdam, Bd. 39, Nr. 47, 19. (Nov. 19, 1998), Seiten 8633–8636, XP004140600 ISSN: 0040–4039.

K C Nicolaou et al: "Total syntheses of Epothilones A and B via a macrolactonization–based strategy" Journal of the American Chemical Society,US,American Chemical Society, Washington, DC, Bd. 119, Nr. 34, 1997, Seiten 7974–7991–7991, XP002110540 ISSN: 0002–7863.

Synlett Letters, "Synthesis of Epothilones: Stereoselective Routes to Epothilone B", Aug. 1998, pp. 861–864.

Letters to Nature, Synthesis of Epothilones A and B in Solid and Solution Phase, May 15, 1997, vol. 387, pp. 268–272.

*Primary Examiner*—Robert Gerstl
(74) *Attorney, Agent, or Firm*—Millen, White, Zelano, Branigan, P.C.

(57) ABSTRACT

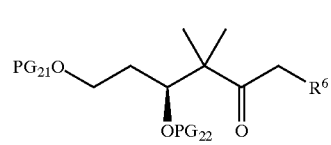

(2)

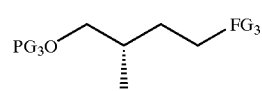

(3)

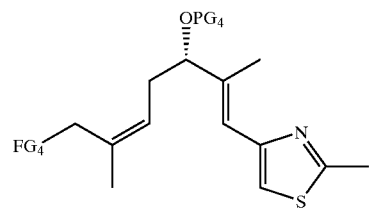

(4)

The invention relates to a method for producing epothilone B and derivatives, and to intermediate products for this method. According to the novel method, the epothilone B or derivatives are produced in high yields from the C1–C6, C7–C10 and C11–C20-fragments 2, 3 and 4 that can be obtained economically and diastereomerically purely (the variable radicals having the meanings given in the description).

18 Claims, No Drawings

METHOD FOR PRODUCING EPOTHILONE B AND DERIVATIVES, AND INTERMEDIATE PRODUCTS FOR THIS METHOD

This application is a 371 of PCT EP99/07746

This invention relates to a process for the production of epothilone B and derivatives as well as intermediate products for this process.

It is known that the natural substances epothilone A (R=H) and epothilone B (R=methyl) (compound I, DE 195 42 986 A1, DE 41 38 042 C2)

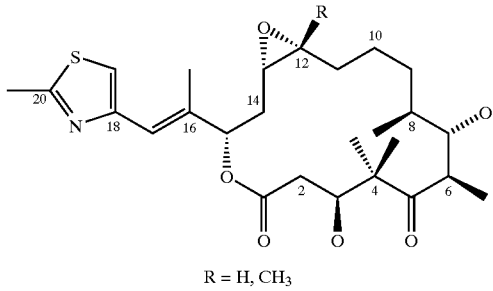

R = H, CH$_3$ have a fungicidal and cytotoxic effect. According to indications for in vitro activity against mammary and intestinal tumor cell lines, this family of compounds appears especially advantageous for the development of a pharmaceutical agent. Various working groups have successfully endeavored to synthesize these macrocyclic compounds. The working groups start from various fragments of the macrocycle to synthesize the desired natural substances.

In any case, diastereomer-pure fragments as starting products and intermediate products are required for a successful epothilone synthesis. Diastereomer purity is often decisive for the action and reliability of a pharmaceutical agent and thus a requirement for its production.

The total synthesis of epothilone A is described by Schinzer et al. in Chem. Eur. J. 1996, 2, No. 11, 1477–1482 and in Angew. Chem. 1997, 109, No. 5, pp. 543–544).

Epothilone derivatives were already described by Höfle et al. in WO 97/19086. These derivatives were produced starting from natural epothilone A or B.

Another synthesis of epothilone and epothilone derivatives was described by Nicolaou et al. in Angew. Chem. 1997, 109, No. 1/2, pp. 170–172. Nicolaou et al. also described the synthesis of epothilone A and B and several epothilone analogs in Nature, Vol. 387, 1997, pp. 268–272, and the synthesis of epothilone A and its derivatives in J. Am. Chem. Soc., Vol. 119, No. 34, 1997, pp. 7960–7973, as well as the synthesis of epothilone A and B and several epothilone analogs in J. Am. Chem. Soc., Vol. 119, No. 34, 1997, pp. 7974–7991.

Nicolaou et al. also describe in Angew. Chem. 1997, 109, No. 19, pp. 2181–2187 the production of epothilone A analogs using combinative solid-phase synthesis. Several epothilone B analogs are also described there.

The object of this invention is to provide a process for the production of epothilone B and derivatives, in which epothilone is built up from fragments that can be obtained at a reasonable price and enantioselectively as starting products.

Another object is the provision of epothilone B or its derivatives in higher yields than according to the previously known processes.

The production of epothilone B according to this invention is based on the linkage of three partial fragments 2, 3, and 4 according to the diagram below:

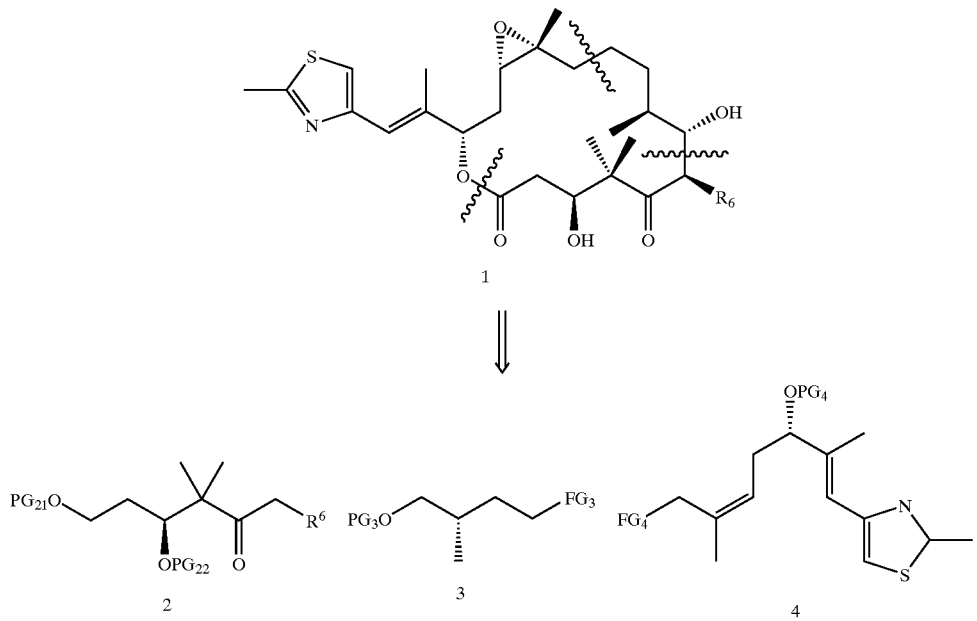

means a C1–C6 fragment (epothilone numbering system) of general formula:

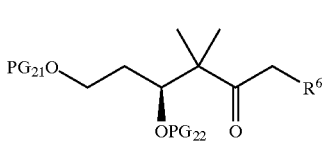

in which
PG$_{21}$ and PG$_{22}$, independently of one another, in each case mean a hydroxy protective group and
R$^6$ means a straight-chain or branched-chain alkyl group with up to 6 carbon atoms, a cycloalkylalkyl group with up to 10 carbon atoms, or a phenyl group, 1- or 2-naphthyl group, heteroaryl group, benzyl group or methylheteroaryl group.

3 stands for a C7–C10 fragment (epothilone numbering system) of general formula:

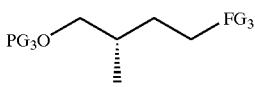

(3)

in which
PG$_3$ means a hydroxy protective group, and
FG$_3$ means a phenylsulfonyl group.

4 stands for a C11–C20 fragment (epothilone numbering system) of general formula:

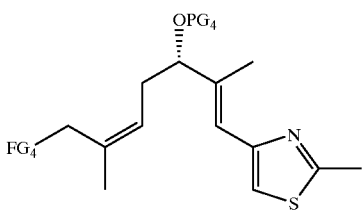

4 in which
FG$_4$ means an iodine atom or another leaving group, and
PG$_4$ means a hydroxy protective group.

Synthesis
Production of 2

According to this invention, partial fragment 2 is obtained with use of the following synthesis route enantioselectively from very reasonably-priced starting compounds in an efficient way with high enantiomer excesses.

The substituents have—unless otherwise indicated—the meanings that are already indicated above in the individual fragments:

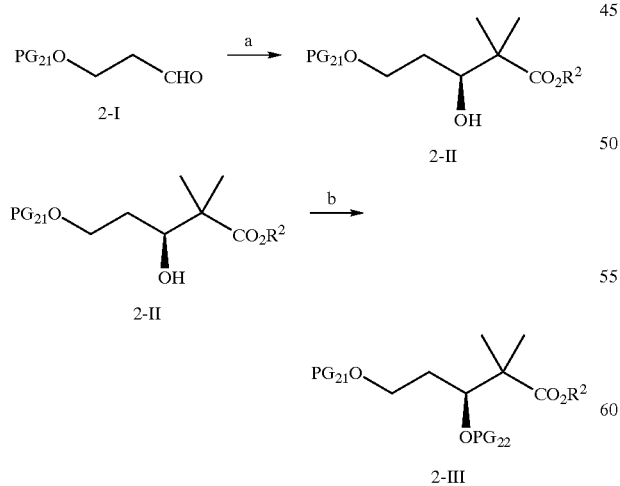

Steps a and b

The protected 3-hydroxypropanal (2-I), which was produced analogously to the literature (Kiyooka et al., J. Org. Chem., 1991, 56, 2276–2278) from 1,3-propanediol by monoprotection and oxidation, is reacted under chiral catalysis with a silylketenacetal of general formula

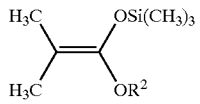

(R$^2$=methyl, ethyl, etc.) with mediation by N-tosylvaline/diborane to form (2-II), with high enantiomeric excess. In compound (2-II), the 3-hydroxy group is then protected according to methods that are known to one skilled in the art for the production of the compound of general formula (2-III).

As alkyl, silyl and acyl radicals for the protective groups PG$_{21}$, PG$_{22}$, PG$_3$ and PG$_4$, the radicals that are known to one skilled in the art are considered. Alkyl or silyl radicals that can be easily cleaved from the corresponding alkyl and silyl ethers, such as, for example, the methoxymethyl, methoxyethyl, ethoxyethyl, tetrahydropyranyl, tetrahydrofuranyl, trimethylsilyl, triethylsilyl, tert-butyl-dimethylsilyl, tert-butyldiphenylsilyl, tribenzylsilyl, triisopropylsilyl, benzyl, para-nitrobenzyl, or para-methoxybenzyl radical, and alkylsulfonyl and arylsulfonyl radicals, are preferred. As acyl radicals, e.g., formyl, acetyl, propionyl, isopropionyl, pivalyl, butyryl or benzoyl, which can be substituted with amino and/or hydroxy groups, are suitable.

A survey on protective groups is found in, e.g., "Protective Groups in Organic Synthesis," Theodora W. Green, John Wiley and Sons.

In this case, those protective groups are preferred that can be cleaved under the action of fluoride, such as, e.g., trimethylsilyl, tert-butyldimethylsilyl, triisopropyl, triethylsilyl, tert-butyldiphenylsilyl radicals, and of the latter especially the tert-butyldimethylsilyl radical, triisopropylsily radical, and the tert-butyldiphenylsilyl radical.

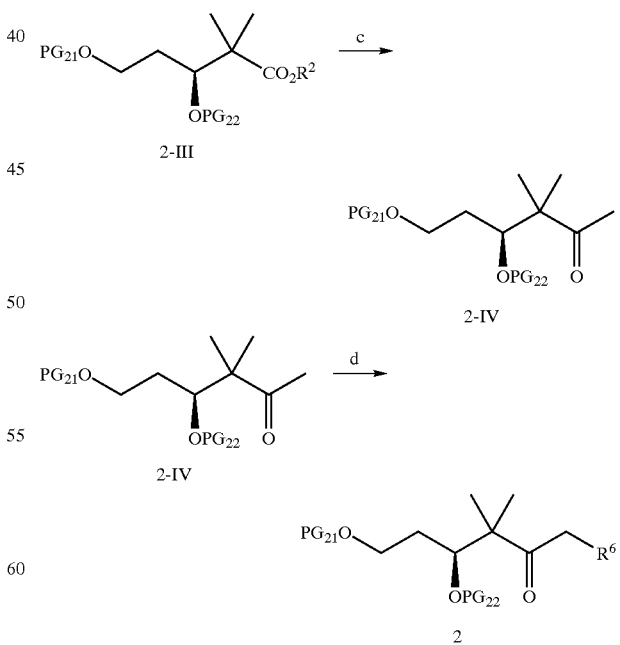

Steps c and d

Compound (2-III) is converted into methylketone (2-IV) by reaction with trimethylsilylmethyllithium and is then reacted to form the compound of general formula 2, according to the methods known to one skilled in the art, with an alkyl, cycloalkylalkyl, aryl, heteroaryl, methylaryl or methylheteroaryl halide of formula (2-X), $R^6$-Hal, in which $R^6$ means a straight-chain or branched-chain alkyl group with up to 6 carbon atoms, a cycloalkylalkyl group with up to 10 carbon atoms, a phenyl group, 1- or 2-naphthyl group, heteroaryl group, benzyl group or methylheteroaryl group, and Hal means a halogen atom (chlorine, bromine or iodine).

As an alternative, compound (2-III) can also be reduced to alcohol, according to methods that are known to one skilled in the art, selectively oxidized to aldehyde and then reacted with an organometallic compound Me-$CH_2$—$R^6$ (Me stands for a lithium atom or for a radical MgHal, Hal=Cl, Br: $R^6$ has the above-indicated meaning). Subsequent oxidation then also yields a compound of general formula 2.

As $C_1$–$C_6$ alkyl groups for $R^6$, for example, a methyl, ethyl, propyl, isopropyl, butyl, isobutyl, tert-butyl, pentyl, isopentyl, neopentyl, or hexyl group is suitable.

For a cycloalkylalkyl group $R^6$ with up to 10 carbon atoms, for example, the cyclopropylmethyl, cyclobutylmethyl, cyclopentylmethyl or cyclohexylmethyl group can be mentioned.

The heteroaryl radical, either as $R^6$ or in methylheteroaryl group $R^6$, can be, for example, a furyl, thienyl, pyridyl, pyrazolyl, pyrimidinyl, oxazolyl, pyridazinyl, pyrazinyl, quinolyl, or thiazolyl radical.

The radicals that are possible above for $R^6$ can be substituted in one or more places by halogen, OH, O-alkyl, $CO_2H$, $CO_2$-alkyl, —$NH_2$, —$NO_2$, —$N_3$, —CN, $C_1$–$C_{20}$ alkyl, $C_1$–$C_{20}$ acyl, or $C_1$–$C_{20}$ acyloxy groups. Heteroatoms in the heteroaryl radicals can be oxidized.

Production of 3

The substituents have—if not otherwise indicated—the meanings that are already indicated above in the individual fragments.

Partial fragment 3 can be produced in high optical purity from the hydroxyisobutyric acid methyl ester that can be obtained inexpensively.

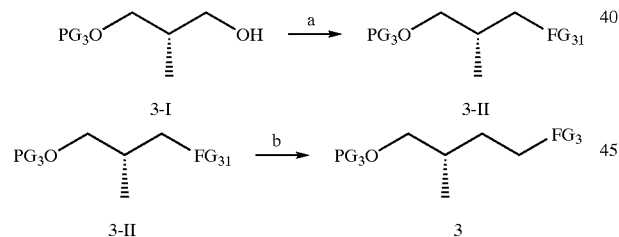

Steps a and b

Compound (3-I) is available in a known way by monoprotection and reduction from the commercially available hydroxyisobutyric acid-methyl ester. Compound (3-I) is reacted with tosyl chloride to form compound (3-II) (thus conversion of the hydroxy group into a better leaving group; instead of the tosyl radical, other conventional leaving groups, such as mesylate, triflate, etc., are also possible); subsequent addition of a methylsulfone anion (within the context of the examples of this invention this is phenylsulfonylmethyl anion) yields a compound of general formula 3.

Production of 4

The substituents have—if not otherwise indicated—the meanings that are already indicated above in the individual fragments.

The partial fragments of formula 4 can be produced in an efficient way with very high optical purity from inexpensive malic acid that can be obtained at a reasonable price.

The synthesis is described below in the example of L-(−)-malic acid.

Starting from D-(+)-malic acid, the corresponding enantiomeric compounds are obtained, or starting from racemic malic acid, the corresponding racemic compounds are obtained.

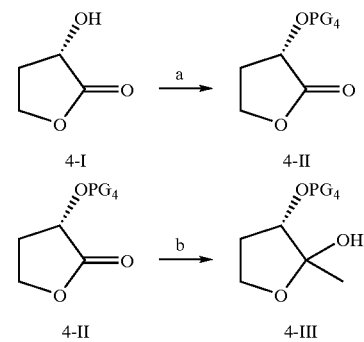

Steps a and b

Compound (4-I) can be obtained commercially or according to known processes from the conventional literature (Green et al., Tetrahedron, 1995, 51, 2865–2874). Compound (4-I) is protected according to the methods that are known to one skilled in the art. As protective groups, the protective groups that are already indicated in more detail above under "Steps a and b" are suitable. In the second step, compound (4-II) is reacted by the addition of methyllithium to form the hemiacetal compound, which is in equilibrium with the open-chain form (4-III).

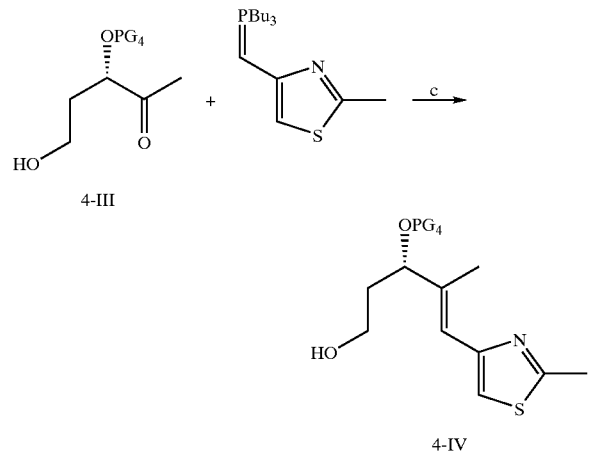

Step c

Compound (4-III) reacts in a highly (E)-stereoselective manner, from the open form that is present in equilibrium, with (2-methyl-thiazol-4-yl-methyl)-tributyl-phosphonium ylide, which was obtained by deprotonation of the corresponding chloride or bromide, to form compound (4-IV).

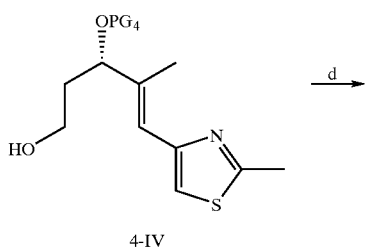

4-IV

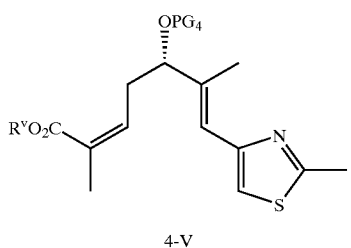

4-V

Step d

After selective oxidation of compound (4-IV) into aldehyde, the latter is converted (Z)-stereospecifically into compound (4-V) according to a method that is known to one skilled in the art with a Still-Genari-Wittig reaction.

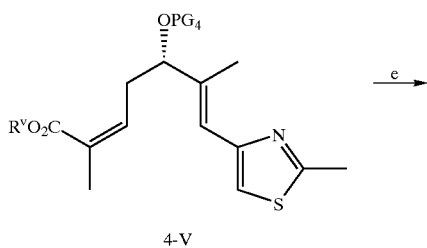

4-V

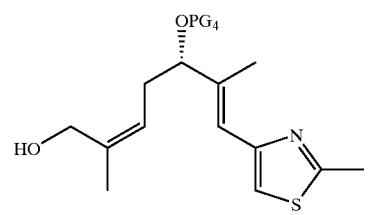

4-VI

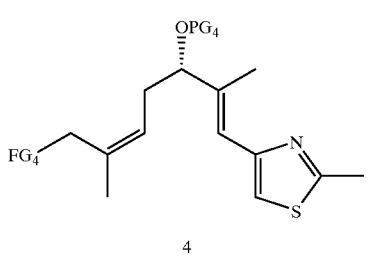

4-VI

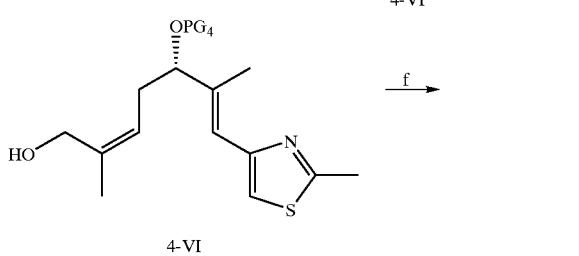

4

Steps e and f

After compound (4-V) is reduced to form allyl alcohol (4-VI), the terminal hydroxyl group is functionalized for the linkage by conversion into a better leaving group, for example into iodide, and yields the compound of general formula 4.

As other leaving groups, for example, the mesylate, tosylate and triflate can be mentioned.

The production of compounds 4-V and 4-VI can also be performed as described in International Patent Application PCT/EP98/04462. Individual fragments 2, 3 and 4 are merged as shown in International Patent Application PCT/EP 98/04462 and are described more precisely below.

First, to this end, the synthesis of a coupling fragment 34-I from individual fragments 3 and 4 is to be performed. This C7–C20 coupling fragment 34-I (epothilone numbering system) is produced by anionic, sulfone-stabilized coupling and subsequent reductive desulfonation.

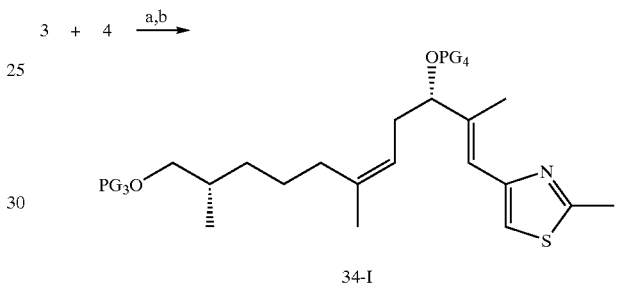

34-I

Steps a and b

After deprotonation of compound 3, it is anionically coupled to compound 4. Subsequent reductive desulfonation according to the methods that are known to one skilled in the art yields the C7–C20 coupling fragment (34-I).

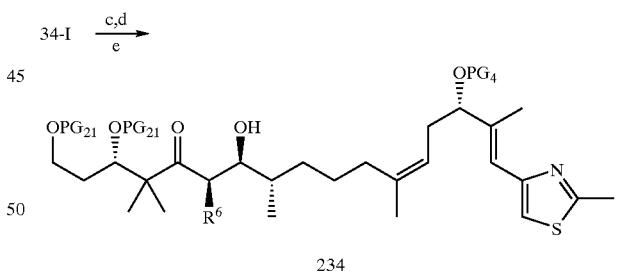

234

Steps c, d and e

After protection of the 7-hydroxy group and protection removal of the primary hydroxyl group (cleavage of $PG_3$) in compound 34-I and selective oxidation into aldehyde, C1–C20 coupling fragment (234) is shown with compound 2 in the form of an aldol reaction.

Epothilone B 1 or a derivative thereof is ultimately produced in 8 additional synthetic stages from compound (234) analogously to the existing literature (K. C. Nicolaou et al., Nature, Vol. 387, 1997, pp. 268–272 and J. Am. Chem. Soc. 1997, 119, pp. 7960–7973).

The examples below are used for a more detailed explanation of the invention, without intending that it be limited thereto:

EXAMPLES A–C

Production of the Compound of Formula 3

Example A (3S)-4-[(1,1-Dimethylethyl)diphenylsilyloxy]-3-methyl-1-phenylsulfonylbutane In 20 ml of absolute pyridine, 6.57 g (20 mmol) of TBDPS-protected (2S)-methylpropane-1,3-diol is mixed with 6.94 g (40 mmol) of tosyl chloride at 0° C., and it is stirred for 3.5 hours (Pyr-HCl salts precipitate out). For working-up, ice is added, and it is stirred for 1 more hour. It is now extracted several times with ether, washed with saturated $NaHCO_3$ solution, dried on $MgSO_4$, filtered and concentrated by evaporation under vacuum in a rotary evaporator.

The crude product that still smells like pyridine is flash-chromatographed on a 10:1-hex/EE-silica gel column. 8.67 g (92.5%) of tosylated product, which was immediately further processed, was obtained.

In 180 ml of absolute THF, 4.34 g (27.9 mmol, 1.5 equivalents) of methylphenylsulfone is mixed at −20° C. with 16.77 ml (26.832 mmol, 1.45 equivalents) of a 1.6 M nBuLi solution and slowly allowed to heat (30 minutes) to room temperature (initially an orange, clear solution becomes cloudy). Now, the tosylate, dissolved in about 20 ml of absolute THF, is added at room temperature and stirred for about 12 more hours.

The violet solution is quenched with saturated $NH_4Cl$ solution and then NaK-tartrate solution is added, until two clear phases are produced. The phases are separated, the aqueous phases are extracted twice more with ether, the combined organic phases are dried on $MgSO_4$ and filtered on a short silica gel frit, rewashed with ether and concentrated by evaporation under vacuum in a rotary evaporator.

After chromatography on a 5:1-hex/EE silica gel column, 7.689 g of the title compound was obtained as a viscous, colorless oil, and also 630 mg of tosylated product, colorless, was obtained. The title compound is thus obtained in 89.1% yield or in 96.0% yield keeping in mind the recovered educt (with the two chemical reactions, thus 82.4% yield or 88.8% yield).

$R_f$-value of tosylated product (hex/EE=3:1)≈0.6 F II (blue), F III (pale blue), $R_f$-value of the title compound (hex/EE=3:1)≈0.39 F II (pale blue);

$^1$H-NMR (400 MHz, $CDCl_3$): δ in ppm=0.84 (d, J=6.4 Hz, 3H, 3-$CH_3$); 0.96 (s, 9H, —$SiC(CH_3)_3$); 1.60 (ddt, $^2J$=12.8 Hz, $J_{2a\text{-}H,3\text{-}H}$=8.9 Hz, $J_{2a\text{-}H,\ 1\text{-}H}$=7.4 Hz, 1H, 2a-H);

1.70 (mc, 1H, 3-H); 1.86 (dddd, $^2J$=12.8 Hz, $J_{2b-H, 3-H}$=8.9 Hz, $J_{2b-H, 1-H}$=7.9 Hz, $J_{2b-H, 1-H}$=5.9 Hz, 1H, 2b-H); 3.09 (mc, 2H, 1-H); 3.36 (dd, $^2J$=9.8 Hz, $J_{4a-H, 3-H}$=6.4 Hz, 1H, 4a-H); 3.44 (dd, $^2J$=9.8 Hz, $J_{4b-H, 3-H}$=5.0 Hz, 1H, 4b-H); 7.37 (m, 6H, $CH_{arom}$); 7.55 (m, 6H, $CH_{arom}$); 7.63 (m, 1H, (Ts)p-$CH_{arom}$); 7.88 (mc, 2H, (Si)p-$CH_{arom}$).

MS (EI): m/e=468 [M+1]; 467 [M]; 460; 425; 414; 383; 382; 326; 267; 252; 213; 182; 136; 57.

Angle of rotation: $[\alpha]_D^{20}$=−5.8; (c=2.01; $CHCl_3$)

$C_{27}H_{34}O_3SSi$: EA: Cld.: C, 69.5%; H, 7.3% (M=466.71 g.mol$^{-1}$) Fnd.: C, 69.37%; H, 7.50%

Example B

(3S)-4-Hydroxy-3-methyl-1-phenylsulfonylbutane

In 140 ml of absolute THF, 7.5 g (16.07 mmol) of the sulfone that is produced according to Example A is mixed with 22 ml (24.105 mmol) of a 1.1 M TBAF solution and stirred for 10 hours at room temperature. The reaction is quenched with saturated $NH_4Cl$ solution, the phases are separated, the aqueous phase is extracted twice more with ether, the combined organic phases are dried on $MgSO_4$, filtered and concentrated by evaporation under vacuum in a rotary evaporator.

After chromatography on a 1:1-hex/EE-silica gel column, 3.21 g (87.5%) of the title compound was obtained as a colorless, viscous oil.

$R_f$-value (hex/EE=1:1)≈0.12 F III (pale blue);

$^1$H-NMR (400 MHz, $CDCl_3$): δ in ppm=0.87 (d, J=6.9 Hz, 3H, 3-$CH_3$); 1.52 (t, $J_{4-OH, 4-H}$=4.9 Hz, 1H, 4-OH); 1.60 (mc, 1H, 2a-H); 1.71 (mc, 1H, 3-H); 1.85 (ddt, $^2J$=12.8 Hz, $J_{2b-H,3-H}$=9.4 Hz, $J_{2b-H, 1-H}$=5.9 Hz, 1H, 2b-H); 3.15 (mc, 2H, 1-H); 3.40 (ddt, 2H, 4-H); 7.55 (mc, 2H, $CH_{arom}$); 7.64 (mc, 1H, $CH_{arom}$); 7.89 (mc, 2H, $CH_{arom}$).

$^{13}$C-NMR (100 MHz, $CDCl_3$): δ in ppm=16.3 (C-5); 26.1 (C-2); 34.6 (C-3); 54.3 (C-1); 67.4 (C-4); 128.0+129.3 (C-7 and C-8); 133.7 (C-9); 139.1 (C-6).

IR (Si film): ν in cm$^{-1}$=3510br; 3063m; 2959s; 2934s; 2878s; 2668w; 1585w; 1447s; 1407m; 1302m; 1041m; 986m; 908m; 789s; 739s.

MS (EI, 70 eV, 100° C.): m/e=227 [M]; 210; 198 (58); 181 (8); 169 (13); 156 (17); 143 (100); 132 (26); 125 (37); 105 (30); 94 (15); 91 (27); 87 (83); 78 (85); 77 (97); 69 (93); 51 (30).

$C_{23}H_{29}NO_4S$: (M=228.30 g.mol$^{-1}$)

Example C

(3S)-4-[(1,1-Dimethylethyl)dimethylsilyloxy]-3-methyl-1-phenylsulfonyl-butane (Compound of Formula 3)

5.548 g (24.3 mmol) of the compound that is produced according to Example B with 3.31 g (2 equivalents, 48.6 mmol) of imidazole are introduced into 30 ml of absolute DMF. 4.75 g (1.3 equivalents, 31.59 mmol) of TBSCl is now slowly added at 0° C. and stirred for 3 hours, whereby the temperature may slowly increase to room temperature.

For working-up, 50 ml of saturated $NH_4Cl$ solution is added at 0° C. and diluted with ether. The phases are separated, the aqueous phase is extracted three more times with ether, the combined organic phases are washed with water, dried on $MgSO_4$, filtered on 3 cm of silica gel and concentrated by evaporation in a vacuum.

Chromatographic purification on a 5:1-hex/EE-silica gel column produced 8.216 g (98.7%) of the title compound.

$^1$H-NMR (400 MHz, $CDCl_3$): δ in ppm=−0.03 (s, 6H, —Si($CH_3$)$_2$); 0.81 (s, 9H), —SiC($CH_3$)$_3$); 0.83 (d, J=6.5 Hz, 3H, 3-$CH_3$); 1.55 (m, 1H, 2a-H); 1.65 (mc, 1H, 3-H); 1.79 (m, 1H, 2b-H); 3.14 (dd, J=9.0 Hz, J=7.0 Hz, 2H, 1-H); 3.31 (dd, $^2J$=10.0 Hz, $J_{4a-H,3-H}$=6.5 Hz, 1H, 4a-H); 3.42 (dd, $^2J$=10.0 Hz, $J_{4b-H,3-H}$=5.0 Hz, 1H, 4b-H); 7.55 (m, 2H, p-$CH_{arom}$); 7.64 (m, 1H, m-$CH_{arom}$); 7.90 (m, 2H, o-$CH_{arom}$).

$^{13}$C-NMR (100 MHz, $CDCl_3$): δ in ppm=−5.5 (Si($CH_3$)$_2$; 16.3 (3-$CH_3$); 18.2 (SiC($CH_3$)$_3$); 25.8 (SiC($CH_3$)$_3$); 26.4 (C-2); 34.6 (C-3); 54.6 (C-1); 67.5 (C-4); 128.1 (o-$CH_{arom}$); 129.2 (m-$CH_{arom}$); 133.5 (p-$CH_{arom}$); 139.1 (i-$CH_{arom}$).

IR (Si-film): ν in cm$^{-1}$=2957s; 1586w; 1447s; 1389m; 1306s; 1106vs; 740s; 689s; 562s.

MS (Fl, 7 kV, 3 mA, 40° C.): m/e=343 ([M]); 310; 288; 287; 286; 285; 252; 224; 202; 182; 166; 125; 110; 78; 58; 57.

Angle of rotation: $[\alpha]_D^{20}$=−6.7; (c=2.64; $CHCl_3$)

$C_{17}H_{30}O_3SSi$ EA: Cld.: C, 59.6%; H, 8.8% (M=342.56 g.mol$^{-1}$) Fnd.: C, 59.38%; H, 8.72%

EXAMPLES D–J

Production of Compound 4

Example D

(3S)-3-[(1,1-Dimethylethyl)dimethylsilyloxy]-oxolan-2-one 3.92 g (38.4 mmol) of (S)-3-hydroxybutyrolactone with 5.23 g (2 equivalents, 76.8 mmol) of imidazole are introduced at 0° C. into 50 ml of absolute DMF. 7.53 g (1.3 equivalents, 49.92 mmol) of TBSCl is now slowly added and stirred for 2.5 hours.

For working-up, it is diluted with 100 ml of ether, and the reaction is quenched by adding 100 ml of saturated $NH_4Cl$ solution. The phases are separated, the aqueous phase is extracted three more times with ether, the combined organic phases are washed with water, dried on $MgSO_4$, filtered on 3 cm of silica gel and concentrated by evaporation in a vacuum.

Chromatographic purification on a 15:1-hex/EE-silica gel column produced 8.272 g (99.6%) of the title compound, as a colorless oil (crystallized at <−20° C.)

$R_f$-value (hex/EE=1:1)≈0.70

$R_f$-value (hex/EE=5:1)≈0.51 F I (blue);

$^1$H-NMR (400 MHz, $CDCl_3$): δ in ppm=0.14 (s, 3H, —Si$CH_3$); 0.17 (s, 3H, —Si$CH_3$); 0.91 (s, 9H, —SiC($CH_3$)$_3$); 2.22 (dddd, J=12.8 Hz, $J_{4-Ha,3-H}$=9.0 Hz, $J_{4-Ha,5-Ha}$=9.0 Hz, $J_{4-Ha, 5-Hb}$=8.6 Hz, 1H, 4-Ha); 2.45 (m, 1H, 4-Hb); 4.19 (td, $J_{5-Ha,4-Ha\ and\ 5-Hb}$=9.0 Hz, $J_{5-Ha,4-Hb}$=6.6 Hz, 1H, 5-Ha); 4.34–4.43 (m, 2H, 5-Hb and 3-H).

$^{13}$C-NMR (100 MHz, $CDCl_3$): δ in ppm=−5.3 (Si$CH_3$); −4.2 (Si$CH_3$); 18.2 (SiC($CH_3$)$_3$); 25.6 (SiC($CH_3$)$_3$); 32.3 (C-4); 64.7 (C-5); 68.2 (C-3); 175.8 (C-2).

IR (Si-Film): ν in cm$^{-1}$=2956s; 2931s; 2887m; 2858s; 1788vs; 1473w; 1464w; 1362w; 1254m; 1220m; 1154vs; 1022s; 999s; 947m; 888m; 840s.

MS (Fl, 7 kV, 3 mA, 20° C.): m/e=217 ([M+1], <1); 161 (4); 160 (11); 159 ([M−tBu], 100); 132 (<1).

Angle of rotation: $[\alpha]_D^{20}$=−30.5; (c=5.82; $CHCl_3$)

$C_{10}H_{20}O_3Si$: (M=216.35 g.mol$^{-1}$)

Example E

(3S)-3-[(1,1-Dimethylethyl)dimethylsilyloxy]-2-methyl-oxolan-2-ol or (3S)-3-[(1,1-dimethylethyl)dimethylsilyloxy]-5-hydroxy-pentan-2-one In 100 ml of absolute THF, 5.27 g (ex 24.34 mmol of (S)-3-hydroxybutyrolactone) of the crude compound of Example D is mixed drop by drop at −78° C. with 18.26 ml ($\geq$1.2 equivalents, 29.216 mmol) of a 1.6 M MeLi solution (in ether, Fluka) and stirred for 90 more minutes. The cooling bath is removed, and the reaction is quenched by the quick but controlled addition of saturated $NH_4Cl$ solution. The reaction solution is allowed to heat to room temperature. It is now mixed with saturated NaK-tartrate solution until two clear phases form. The solution is diluted with ether, the phases are separated, the aqueous phase is extracted twice more with ether, the combined organic phases are dried on $MgSO_4$, filtered and concentrated by evaporation in a vacuum.

Chromatographic purification on a 10:1–5:1-hex/EE gradient-silica gel column produced 4.958 g (87.7% over the two stages) of the title compound(s) as a colorless, crystalline compound.

Owing to this equilibrium and the diastereomer mixture, a complete characterization of the product is not possible.

$R_f$-value (hex/EE=5:1)≈0.22 F I (blue); F III (green);

MS (FI, 7 kV, 3 mA, 20° C.): m/e=214 ([M–$H_2O$]); 203; 189; 176; 175 ([M–tBu]); 157; 132.

$C_{11}H_{24}O_3Si$: EA: Cld.: C, 56.9%; H, 10.4% (M=232.39 g.mol$^{-1}$) Fnd.: C, 57.15%; H, 10.34%

Example F

4-Chloromethyl-2-methyl thiazole

A solution of 1,3-dichloropropan-2-one (4.82 g, 38 mmol) and thioacetamide (7.5 g, 0.1 mol) in anhydrous ethanol (70 ml) was heated to boiling under argon for 5.5 hours and then concentrated by evaporation in a vacuum. The dark-colored crystalline residue was dissolved in water (about 250 ml), the aqueous solution was washed several times with diethyl ether and brought to pH≈8 by adding $NaHCO_3$ and then shaken out with diethyl ether (four times 100 ml). The dried, dark organic phase was filtered on a frit coated with silica gel, rewashed with hex/EE (3:1) and concentrated by evaporation.

The residue was purified by bulb tube distillation (bath temperature: 90–95° C., 10 Torr). 11.91 g (81%) of the title compound was obtained as a light yellowish, skin-irritating oil.

Example G

(2-Methyl thiazol-4-yl)-methyl-tri-n-butyl-phosphonium chloride

Tri-n-butylphosphane (38 ml, 0.156 mol) was added to a solution of 4-chloromethyl-2-methylthiazole (23 g, 0.156 mol) in anhydrous benzene (200 ml) under argon, and the solution was heated to boiling for 8 hours. Then, it was concentrated by evaporation in a vacuum, the residue was dried for 30 more minutes at 0.01 Torr, and the phosphonium salt was brought to crystallization by trituration with dry diethyl ether. 53 g (97%) of the title compound was obtained as colorless, hygroscopic crystals.

A sample under analysis was converted with aqueous KBr solution into the corresponding bromide and purified by flash chromatography on silica gel (EE/MeOH, 4:1) (melting point: 102–105° C.)

$^1$H-NMR (400 MHz, $CDCl_3$): δ in ppm=0.86 (t, $J_{HH}$=7.0 Hz, 9H, $CH_2CH_3$); 1.35–1.50 (m, 12H, $CH_2$); 2.35 (mc, 6H, P—$CH_2$—R); 2.59 (s, 3H, 2-$CH_3$); 4.28 (d, $^2J_{HP}$=14.6 Hz, 2H, P—$CH_2$-TAr); 7.65 (d, $^4J_{HP}$=3.5 Hz, 1H, 5-H).

$^{13}$C-NMR (100 MHz, $CDCl_3$): δ in ppm=13.2 (—$CH_2CH_3$); 19.0 (2-$CH_3$); 19.0 ($^1J_{PC}$=46.8 Hz, P—$CH_2$—R); 22.6 ($^1J_{PC}$=47.4 Hz, P—$CH_2$-TAr); 23.4 ($J_{PC}$=5.4 Hz, —$CH_2$—); 23.8 ($J_{PC}$=15.3 Hz, —$CH_2$—); 119.8 ($^3J_{PC}$=9.2 Hz, C-5); 142.9 ($^2J_{PC}$=9.9 Hz, C-4); 166.7 ($^4J_{PC}$=1.5 Hz, C-2).

Example H

(3S,4E)-3-[(1,1-Dimethylethyl)dimethylsilyloxy]-4-methyl-5-(2-methylthiazol-4-yl)pent-4-enol 16.8 g (48.0 mmol) of the compound that is produced according to Example G is deprotonated in 200 ml of absolute THF at −78° C. with a solution of 1.1 equivalents, NaHMDS/KHMDS (about 1:1), dissolved in 70 ml of absolute THF. After 40 minutes, 4.914 g (21.145 mmol) of the compound that is produced according to Example E and that is dissolved in 20 ml of absolute THF is slowly added.

After 1 hour at −78° C. (virtually no conversion), the cooling bath is removed, heated to about 40° C. and stirred for 20 more minutes.

For working-up, it is diluted with 100 ml of ether and quenched by adding 250 ml of saturated $NH_4Cl$ solution. Then, the phases are separated, the aqueous phase is extracted three more times with ether, the combined organic phases are dried on $MgSO_4$, filtered and concentrated by evaporation.

2× chromatographic purification on a 3:1-hex/EE-silica gel column produced a total of 559 mg (still slightly contaminated) product and 4.9 g of the title compound (yield 78.8% at a 1:9 ratio) as viscous, colorless oils, which crystallizes in a deep-freezing device (<−20° C.). (In the case of the compound, the nonpolar compound is not the expected DB-isomer, but rather the C1-silylated compound based on a silyl shift under the reaction conditions.)

$R_f$-value (hex/EE=3:1) of nonpolar both F I (blue); product≈0.32

$R_f$-value (hex/EE=3:1) of the title compound≈0.21

$^1$H-NMR (400 MHz, $CDCl_3$) of nonpolar product: δ in ppm=0.068 (s, 3H, —$SiCH_3$); 0.072 (s, 3H, —$SiCH_3$); 0.90 (s, 9H, —$SiC(CH_3)_3$); 1.82 (m, 2H, 2-H); 2.02 (s, 3H, 4-$CH_3$); 2.69 (s, 3H, TAr—$CH_3$); 3.46 (d, J=2.5 Hz, 1H, 3-OH); 3.79–3.90 (m, 2H, 1-H); 4.36 (t, J=6.0 Hz, 1H, 3-H); 6.59 (s, 1H, 5-H); 6.91 (s, 1H, TAr—$CH_{arom}$).

$^{13}$C-NMR (100 MHz, $CDCl_3$) of nonpolar product: δ in ppm=−5.53 ($SiCH_3$); −5.51 ($SiCH_3$); 14.8 (4-$CH_3$); 18.1 ($SiC(CH_3)_3$); 19.2 (TAr—$CH_3$); 25.9 ($SiC(CH_3)_3$); 37.1 (C-2); 62.2 (C-1); 76.9 (C-3); 115.3 (C-7); 118.2 (C-5); 141.8 (C-4); 153.2 (C-6); 164.4 (C-8).

Angle of rotation: $[\alpha]_D^{20}$=−7.5; (c=2.3; $CHCl_3$)

$C_{16}H_{29}NO_2SSi$: EA: Cld.: C, 58.7%; H, 8.9%; N,4.3% (M=327.55 g.mol$^{-1}$) Fnd.: C, 58.48%; H, 8.85%; N,4.41%

$^1$H-NMR (400 MHz, $CDCl_3$) of the title compound: δ in ppm=0.01 (s, 3H, —$SiCH_3$); 0.07 (s, 3H, —$SiCH_3$); 0.88 (s, 9H, —$SiC(CH_3)_3$); 1.73–1.90 (m, 2H, 2-H); 1.98 (s, 3H, 4-$CH_3$); 2.28 (t, J=5.0 Hz, 1H, 1-OH); 2.67 (s, 3H, TAr—$CH_3$); 3.71 (m, 2H, 1-H); 4.35 (dd, $J_{3-H,2'-H}$=7.5 Hz, $J_{3-H,2-H}$=4.5 Hz, 1H, 3-H); 6.49 (s, 1H, 5-H); 6.89 (s, 1H, TAr—$CH_{arom}$).

$^{13}$C-NMR (100 MHz, CDCl$_3$) of the title compound: δ in ppm=−4.8 (SiCH$_3$); −4.2 (SiCH$_3$); 14.7 (4-CH$_3$); 18.5 (SiC(CH$_3$)$_3$); 19.6 (TAr—CH$_3$); 26.2 (SiC(CH$_3$)$_3$); 38.7 (C-2); 60.6 (C-1); 77.7 (C-3); 115.7 (C-7); 119.2 (C-5); 142.0 (C-4); 153.4 (C-6); 164.9 (C-8).

IR (Si film): ν in cm$^{-1}$=3385br; 2954vs; 2928vs; 2885m; 2856s; 1655w; 1508w; 1472m; 1462m; 1440w; 1388w; 1360w; 1255m; 1184w; 1098vs; 1027s; 1005s; 978m; 939w; 884m; 837vs; 777vs; 738m.

MS (Fl, 7 kV, 3 mA, 20° C.): m/e=327 ([M]); 270; 269; 223, 222; 215; 197; 195; 175; 165; 133; 132; 113; 112.

Angle of rotation: $[α]_D^{20}$=−31.5; (c=2.81; CHCl$_3$)

C$_{16}$H$_{29}$NO$_2$SSi: (M=327.55 g.mol$^{-1}$)

Example I (5S,2Z,6E)-2,6-Dimethyl-5-[(1,1-dimethylethyl)-dimethylsilyloxy]-7-(2-methylthiazol-4-yl)hepta-2,6-dienoic acid ethyl ester In 150 ml of absolute CH$_2$Cl$_2$, 1.57 ml (1.2 equivalents, 17.95 mmol) of oxalyl chloride is slowly mixed at −78° C. with 2.66 ml (2.5 equivalents, 37.4 mmol) of DMSO and stirred for 10 more minutes. 4.9 g (14.96 mmol) of the compound that is produced according to Example H and dissolved in 20 ml of absolute CH$_2$Cl$_2$ is now slowly added in drops. After 45 minutes, 12.8 ml (5 equivalents, 74.8 mmol) of Hünig base is added, the cooling bath is removed, and the temperature of the reaction solution is allowed to increase to room temperature over a period of 1 hour. It is now diluted with ether, quenched with saturated NH$_4$Cl solution, the phases are separated, the organic phase is washed successively with water, saturated NaHCO$_3$ solution, water and brine, dried on MgSO$_4$, filtered and concentrated by evaporation in a vacuum.

After extensive drying under high vacuum (about 0.1 mbar), the crude aldehyde is immediately used.

6.73 g (≧1.3 equivalents, 19.455 mmol) of 2-phosphonopropionic acid-(trifluoro)-triethylester and 11.87 g (M=264.32 g.mol$^{-1}$; ≧3 equivalents, 44.91 mmol) of 18-crown 6 are introduced at −78° C. into 200 ml of absolute THF. It is now deprotonated by the slow addition of 3.614 g (M=199.49 g.mol$^{-1}$; 1.15 equivalents, 17.21 mmol, 95% KHMDS) of KHMDS, dissolved in some absolute THF, and it is stirred for 15 more minutes, whereby the cooling bath is removed briefly. Then, the crude aldehyde, dissolved in about 45 ml of absolute THF, is slowly added over a period of 70 minutes and stirred for 30 more minutes. The cooling bath is removed; and the reaction is quenched by adding saturated NH$_4$Cl solution.

After phase separation, it is washed with saturated NaHCO$_3$ solution, the aqueous phases are extracted twice more with ether, and the combined organic phases are dried on magnesium sulfate. After the organic phases are filtered on a short silica gel frit, it is concentrated by evaporation in a vacuum. Chromatographic purification on a 15:1–10:1-hex/EE-gradient silica gel column produced 5.453 g (89%) of the title compound as a single double-bond isomer.

R$_f$-value (hex/EE=3:1)≈0.63 F III (very pale blue);

R$_f$-value (hex/EE=5:1)≈0.46 F II (blue);

$^1$H-NMR (400 MHz, CDCl$_3$): δ in ppm=0.01 (s, 3H, —SiCH$_3$); 0.04 (s, 3H, —SiCH$_3$); 0.88 (s, 9H, —SiC(CH$_3$)$_3$); 1.28 (t, J=7.0 Hz, 3H, —CO$_2$CH$_2$CH$_3$); 1.88 (s, 3H, 2-CH$_3$); 2.00 (s, 3H, 6-CH$_3$); 2.70 (s, 3H, TAr—CH$_3$); 2.75 (m, 2H, 4-H); 4.18 (q, J=7.0 Hz, 2H, —CO$_2$CH$_2$CH$_3$); 4.21 (t, J=5.5 Hz, 1H, 5-H); 5.98 (td, J$_{3-H,4-H}$=7.3 Hz, $^4$J$_{3-H,2-CH3}$=1.5 Hz, 1H, 3-H); 6.49 (s, 1H, 7-H); 6.91 (s, 1H, TAr—CH$_{arom}$).

$^{13}$C-NMR (100 MHz, CDCl$_3$): δ in ppm=−5.1 (SiCH$_3$); −4.7 (SiCH$_3$); 14.1 (12-CH$_3$); 14.3 (CO$_2$CH$_2$CH$_3$); 18.2 (SiC(CH$_3$)$_3$); 19.2 (TAr—CH$_3$); 20.7 (2-CH$_3$); 25.8 (SiC(CH$_3$)$_3$); 36.6 (C-4); 60.1 (CO$_2$CH$_2$CH$_3$); 77.9 (C-5); 115.2 (C-9); 118.8 (C-7); 128.3 (C-2); 139.0 (C-3); 141.9 (C-6); 153.2 (C-8); 164.4 (C-10); 168.0 (CO$_2$Et).

IR (Si film): ν in cm$^{-1}$=2956vs; 2929vs; 2896m; 2856s; 1714vs; 1648w; 1506w; 1472m; 1462m; 1372m; 1252s; 1210s; 1185m; 1132s; 1096vs; 1032m; 951w; 837vs; 808m; 777s; 737w.

MS (Fl, 7 kV, 3 mA, 40° C.): m/e=410 ([M]); 352; 336; 297; 282; 253; 224; 167; 132; 127; 57.

C$_{21}$H$_{35}$NO$_3$SSi: EA: Cld.: C, 61.6%; H, 8.6%; N,3.4% (M=409.65 g.mol$^{-1}$) Fnd.: C, 61.55%; H, 8.53%; N,3.39%

Example J (5S,2Z,6E)-2,6-Dimethyl-5-[(1,1-dimethylethyl)-dimethylsilyloxy]-7-(2-methylthiazol-4-yl)hepta-2,6-dienol (Compound of Formula 4)

In 250 ml of absolute THF, 5.43 g (13.255 mmol) of the compound, produced according to Example 1, is mixed at 0° C. drop by drop with 40 ml of a 1M DIBAH solution (in heptane). After 2.5 hours, quenching is done with 3 ml of MeOH at 0° C. to stop the reaction, and after dilution with diethyl ether, 200 ml of semi-concentrated NaK-tartrate solution is added. After about 45 vigorous stirring at room temperature, the two clear phases are separated, the aqueous phase is extracted twice more with ether, and the combined organic phases are dried on magnesium sulfate, filtered and concentrated by evaporation. Chromatographic purification on a 5:1-hex/EE-silica gel column produced 4.752 g (97.5%) of the title compound as a viscous, colorless oil, which crystallizes in a deep-freezing device.

R$_f$-value (hex/EE=3:1)=0.24 F III (intense violet);

$^1$H-NMR (400 MHz, CDCl$_3$): δ in ppm=0.02 (s, 3H, —SiCH$_3$); 0.04 (s, 3H, —SiCH$_3$); 0.88 (s, 9H, —SiC(CH$_3$)$_3$); 1.79 (s, 3H, 2-CH$_3$); 2.00 (d, $^4$J=1.0 Hz, 3H, 6-CH$_3$); 2.20 (t, J=6.0 Hz, 1H, 1-OH); 2.22 (m, 1H, 4-H); 2.46 (dt, J=14.1 Hz, J=8.0 Hz, 1H, 4-H); 2.69 (s, 3H, TAr—CH$_3$); 4.00 (dd, J=12.0 Hz, J=6.5 Hz, 1H, 1-H); 4.12 (dd, J=12.0 Hz, J=5.0 Hz, 1H, 1-H); 4.13 (dd, J=11.0 Hz, J=5.0 Hz, 1H, 5-H); 5.30 (td, J=8.0 Hz, J=2.5 Hz, 1H, 3-H); 6.43 (s, 1H, 7-H); 6.91 (s, 1H, TAr—CH$_{arom}$).

$^{13}$C-NR (100 MHz, CDCl$_3$): δ in ppm=−4.9 (Si(CH$_3$)$_2$); −4.7 (Si(CH$_3$)$_2$); 14.2 (6-CH$_3$); 18.3 (SiC(CH$_3$)$_3$); 19.2 (TAr—CH$_3$); 22.0 (2-CH$_3$); 25.8 (SiC(CH$_3$)$_3$); 35.4 (C-4); 61.9 (C-1); 78.2 (C-5); 115.2 (C-9); 118.8 (C-7); 124.3 (C-3); 137.6 (C-2); 142.2 (C-6); 152.9 (C-8); 164.6 (C-10).

IR (Si film): ν in cm$^{-1}$=3333br; 2956s; 2927s; 2856s; 1657w; 1508w; 1472m; 1462m; 1441m; 1253s; 1185w; 1100vs; 1006s; 938m; 887m; 836s; 776s; 737m.

MS (Fl, 7 kV, 3 mA, 35° C.): m/e=368 ([M+1]); 367 ([M]); 365; 309; 285; 282; 252; 237; 235; 224; 167; 132; 115; 85; 75; 58; 57.

Angle of rotation: $[\alpha]_D^{20}$=−6.8; (c=2.20; CHCl$_3$)

C$_{19}$H$_{33}$NO$_2$SSi: (M=367.62 g.mol$^{-1}$)

EXAMPLES K–L

Production of Compound 34-I

Example K (2S,4R,6Z,9S,10E)-1,9-Bis[(1,1-dimethylethyl) dimethylsilyloxy]-11-(2-methylthiazol-4-yl)-4-phenylsulfonyl-2,6,10-trimethyl-undeca-6,10-diene In 100 ml of absolute CH$_3$CN/ether (3:2), 4.66 g (12.676 mmol) of the compound, produced according to Example J, is introduced in succession with 4.324 g (16.479 mmol, 1.3 equivalents) of Ph$_3$P and 1.164 g (17.113 mmol, 1.35 equivalents) of imidazole. 4.625 g (17.746 mmol, 1.4 equivalents) of iodine is slowly added to this solution and stirred for 60 more minutes at room temperature.

For working-up, 400 ml of cold ether is added (formation of precipitate), filtered, and the filtrate is washed three times with saturated Na$_2$S$_2$O$_3$ solution. The organic phase is then dried on MgSO$_4$, filtered on silica gel and concentrated by evaporation. The crude product is dried in a light-free environment in an oil pump vacuum (about 0.1 mbar) and used in the subsequent reaction.

5.645 g (12.676 mmol, 1.3 equivalents) of the compound, produced according to Example C, with 6.7 g (25.35 mmol, 2 equivalents) of 18-crown 6 are introduced at −78° C. into 350 ml of absolute THF and slowly mixed with a solution of 3.59 g (17.113 mmol, 1.35 equivalents, 95% KHMDS) of KHMDS, in some absolute THF. After 60 minutes, the crude allyl iodide, dissolved in 60 ml of absolute THF, is added drop by drop at −78° C. After 60 minutes, the cooling bath is removed, diluted with 250 ml of ether, and the reaction is quenched by adding 250 ml of saturated NH$_4$Cl solution. The phases are separated, the aqueous phase is extracted once more with ether, the combined organic phases are washed twice more with saturated Na$_2$S$_2$O$_3$ solution, then dried on MgSO$_4$, filtered on 2 cm of silica gel and concentrated by evaporation.

2× chromatographic purification on a 10:1–5:1-hex/EE-gradient silica gel column and a 10:1-hex/EE-silica gel column produced 8.185 g of the title compound, as a diastereoisomer mixture, also with some educt (Example C), which can be separated on an MC-silica gel column.

R$_f$-value (hex/EE=3:1)≈0.54 F III (intense violet);

IR (Si film): ν in cm$^{-1}$=2957vs; 2885vs; 2855vs; 1506m; 1472s; 1462s; 1447s; 1388m; 1361m; 1305s; 1256s; 1184m; 1145vs; 1102vs; 1027m; 1006m; 939s; 911s; 837vs; 775vs; 737vs; 691m; 668w.

MS (Fl, 7 kV, 3 mA, 150° C.): m/e=694 ([M+2]); 693 ([M+1]); 692 ([M], 100); 636; 550; 431; 410 (<1); 282 (3); 267; 159(2); 142; 132; 115; 114.

C$_{36}$H$_{71}$NO$_4$S$_2$Si$_2$: (M=692.17 g.mol$^{-1}$)

Example L (2S,6Z,9S,10E)-1,9-Bis[(1,1-dimethylethyl) dimethylsilyloxy]-11-(2-methylthiazol-4-yl)-2,6,10-trimethyl-undeca-6,10-diene (Compound of Formula 34-I)

580 mg (0.838 mmol) of the compound, produced according to Example K, is introduced at −15° C. with 175 mg (1.232 mmol) of Na$_2$HPO$_4$ into 12 ml of MeOH/THF (2:1). 1.466 g (3.189 mmol) of 5% sodium amalgam is now added, the cooling bath is removed after 30 minutes, and the temperature of the reaction solution increases to room temperature over a period of 90 minutes. For working-up, it is filtered and rewashed with ether and water. The filtered solution is washed with saturated NH$_4$Cl solution, dried on MgSO$_4$, filtered on 1 cm of silica gel and concentrated by evaporation in a vacuum.

Chromatographic purification on a 25:1-hex/EE-silica gel column produced 300 mg (64.9%) of the title compound as a colorless oil.

R$_f$-value (hex/EE=5:1)≈0.74

$^1$H-NMR (400 MHz, CDCl$_3$): δ in ppm=0.008 (s, 3H, —SiCH$_3$); 0.02 (s, 6H, —Si(CH$_3$)$_2$); 0.04 (s, 3H, —SiCH$_3$); 0.85 (d, J=6.5 Hz, 3H, 2-CH$_3$); 0.88 (s, 18H, —SiC(CH$_3$)$_3$'s); 1.29–1.39 (m, 3H); 1.65 (s, 3H, 6-CH$_3$); 1.97 (m, 2H); 1.99 (s, 3H, 10-CH$_3$); 2.24 (m, 2H, 8-H); 2.70 (s, 3H, TAr—CH$_3$); 3.33 (dd, J=9.5 Hz, J=6.5 Hz, 1H, 1-H); 3.43 (dd, J=9.5 Hz, J=5.5 Hz, 1H, 1-H); 4.07 (dd, J$_{9-H,8-H}$=J$_{9-H,8'-H}$=6.5 Hz, 1H, 9-H); 5.12 (dd, J$_{7-8,8-H}$=J$_{7-H,8'-H}$=6.5 Hz, 1H, 7-H); 6.44 (s, 1H, 11-H); 6.90 (s, 1H, TAr—CH$_{arom}$).

$^{13}$C-NMR (100 MHz, CDCl$_3$): δ in ppm=−5.4 (SiCH$_3$); −4.7 (SiCH$_3$); 13.9 (10-CH$_3$); 16.7 (2-CH$_3$); 18.6 (2-SiC(CH$_3$)$_3$); 19.2 (TAr—CH$_3$); 23.5 (6-CH$_3$); 25.8 (C-8); 25.9 (SiC(CH$_3$)$_3$); 26.0 (SiC(CH$_3$)$_3$); 32.3 (C-4); 33.2 (C-3); 35.3 (C-5); 35.8 (C-2); 68.4 (C-1); 79.1 (C-9); 114.9 (C-13); 118.7 (C-11); 121.4 (C-7); 136.9 (C-6); 142.6 (C-10); 153.3 (C-12); 164.3 (C-14).

IR (Si film): ν in cm$^{-1}$=2956s; 2928s; 2856s; 1472m; 1462m; 1388w; 1360w; 1255m; 1183w; 1097vs; 1006w; 940m; 836s; 775s.

MS (Fl, 7 kV, 3 mA, 110° C.): m/e=553 ([M+1]); 552 ([M], 100); 495 ([M−tBu]); 463; 417; 365; 283 (8); 282 (33); 269 (2); 224; 167; 159; 115 (<1.

Angle of rotation: $[\alpha]_D^{20}$=+8.4; (c=4.35; CHCl$_3$)

C$_{30}$H$_{57}$NO$_2$SSi$_2$: EA: Cld.: C, 65.3%; H, 10.4%; N,2.5% (M=552.01 g.mol$^{-1}$) Fnd.: C, 65.51%; H, 10.23%; N,2.58%

EXAMPLES M-T

Production of Compound 2

Example M

N-Tosyl-D-valine

A solution of tosyl chloride (20 g, 0.1 mol) in diethyl ether (100 ml) was added in drops at room temperature to a solution of D-valine (11.7 g, 0.1 mol) in 200 ml of 1N NaOH, and the two-phase mixture was stirred vigorously for 4 hours. Then, the diethyl ether phase was separated, the aqueous phase was washed twice more with diethyl ether and acidified at 0° C. by adding concentrated HCl. After 30 minutes, it was suctioned off, liberally rewashed with ice water and dried for several hours at 0.01 Torr. 18.1 g, (67%), of colorless crystals was obtained (melting point: 147° C.).

Example N (3S)-5-[(1,1-Dimethylethyl)dimethylsilyloxy]-2,2-dimethyl-3-hydroxy-pentanoic acid-methyl ester In 50 ml of absolute CH$_2$Cl$_2$, 1.355 g (5 mmol) of the compound, produced according to Example M, under argon is mixed slowly (30 minutes) at room temperature with 5 ml of a 1M BH$_3$-THF complex solution (in THF) and stirred for 20 more minutes (cat. formation).

The solution is cooled to −78° C., and mixed in succession with 940 mg (5 mmol) of TBS-protected 3-hydroxypropanal and 960 mg (5.5 mmol, 1.1 equivalents) of 1-methoxy-2-methyl-1-(trimethylsilyloxy)-prop-1-ene, in each case dissolved in 5 ml of absolute $CH_2Cl_2$.

After 4 hours, it is quenched with 35 ml of phosphate buffer (pH=6.9), the phases are separated, the aqueous phase is shaken out three more times with $CH_2Cl_2$ (20 ml each), the combined organic phases are then dried on $MgSO_4$, filtered and concentrated by evaporation. The residue is taken up with cold hexane for recovery of N-tosyl-D-valine, filtered (about 96% of cat. recovered) and concentrated by evaporation.

Chromatographic purification on a 15:1-hex/EE-silica gel column produced 1.248 g (88%) of the title compound as a colorless oil.

$R_f$-value (hex/EE=5:1)≈0.39 F I (blue);

$^1$H-NMR (400 MHz, $CDCl_3$): δ in ppm=0.06 (s, 6H, —Si($CH_3$)$_2$); 0.88 (s, 9H, —SiC($CH_3$)$_3$); 1.15 (s, 3H, 2-$CH_3$); 1.19 (s, 3H, 2-$CH_3$); 1.57 (ddd, J=11.0 Hz, J=5.5 Hz, J=1.0 Hz, 2H, 4-H); 3.37 (d, J=3.5 Hz, 1H, 3-OH); 3.68 (s, 3H, —$CO_2CH_3$); 3.80 (m, 1H, 5-Ha); 3.87 (dd, J=10.0 Hz, J=5.0 Hz, 1H, 5-Hb); 3.92 (m, 1H, 3-H).

$^{13}$C-NMR (100 MHz, $CDCl_3$): δ in ppm=−5.5 (Si($CH_3$)$_2$); 18.2 (SiC($CH_3$)$_3$); 20.6 (2-$CH_3$); 21.3 (2-$CH_3$); 25.9 (SiC($CH_3$)$_3$); 33.7 (C-4); 47.1 (C-2); 51.8 ($CO_2CH_3$); 62.6 (C-5); 76.0 (C-3); 177.8 (C-1).

IR (Si film): ν in cm$^{-1}$=3630br; 2955s; 2931s; 2884m; 2858s; 1733s; 1472m; 1435w; 1389w; 1257s; 1193m; 1138s; 1099vs; 1006w; 985w; 884w; 838vs.

MS (Fl, 7 kV, 3 mA, 20° C.): m/e=291 ([M]); 261; 235 (4); 234 (15); 233 ([M−tBu], 100); 189; 131; 102.

Angle of rotation: $[\alpha]_D^{20}$=+3.0; (c=1.88; $CHCl_3$)

$C_{14}H_{30}O_4Si$: EA: Cld.: C, 57.9%; H, 10.4% (M=290.47 g.mol$^{-1}$) Fnd.: C, 58.26%; H, 10.31%

Example O (3S)-3,5-[(1,1-Dimethylethyl)dimethylsilyloxy]-2,2-dimethyl-pentanoic acid methyl ester 5.32 g (18.315 mmol) of the compound, produced according to Example N, is introduced at 0° C. with 6.38 ml of 2,6-lutidine (3 equivalents) into 100 ml of absolute $CH_2Cl_2$. 5.05 ml (1.2 equivalents) of TBS triflate is now slowly added in drops. After 3 hours at 0° C., the cooling bath is removed, and the reaction is quenched by adding 25 ml of saturated $NH_4Cl$ solution.

The phases are separated, the aqueous phase is extracted twice more with $CH_2Cl_2$, the combined organic phases are then dried on $MgSO_4$, filtered on 5 cm of silica gel and concentrated by evaporation.

After drying in an oil pump vacuum (about 0.1 mbar), NMR-clean product was already obtained, which was purified chromatographically for analysis on a 3%, and then later 5%, ether on a hexane-silica gel column. 7.123 g (96.1%) of the title compound was obtained as a colorless oil.

$R_f$-value (hex/EE=10:1)≈0.33 F I (blue);

$^1$H-NMR (400 MHz, $CDCl_3$): δ in ppm=0.02 (s, 3H, —$SiCH_3$); 0.03 (s, 3H, —$SiCH_3$); 0.033 (s, 3H, —$SiCH_3$); 0.07 (s, 3H, —$SiCH_3$); 0.86 (s, 9H, —SiC($CH_3$)$_3$); 0.89 (s, 9H, —SiC($CH_3$)$_3$); 1.08 (s, 3H, 2-$CH_3$); 1.15 (s, 3H, 2-$CH_3$); 1.59 (m, 2H, 4-H); 3.62 (m, 2H, 5-H); 3.64 (s, 3H, —$CO_2CH_3$); 4.05 (dd, J=7.5 Hz, J=3.0 Hz, 1H, 3-H).

$^{13}$C-NMR (100 MHz, $CDCl_3$): δ in ppm=−5.3 (Si($CH_3$)$_2$); −4.3 ($SiCH_3$); −3.9 ($SiCH_3$); 18.3 (SiC($CH_3$)$_3$); 20.4 (2-$CH_3$); 21.7 (2-$CH_3$); 25.9 (SiC($CH_3$)$_3$); 26.0 (SiC($CH_3$)$_3$); 36.9 (C-4); 48.3 (C-2); 51.6 ($CO_2CH_3$); 60.3 (C-5); 73.4 (C-3); 177.6 (C-1).

IR (Si film): ν in cm$^{-1}$=2955s; 2930s; 2886m; 2858s; 1736s; 1472m; 1464m; 1434w; 1388w; 1257s; 1135m; 1039w; 1006w; 939w; 837vs.

MS (Fl, 7 kV, 3 mA, 20° C.): m/e=405 ([M], 1); 349 (9); 348 (23); 347 ([M−tBu], 100); 303; 267; 233 (1); 220; 199; 159; 132; 115 (2).

Angle of rotation: $[\alpha]_D^{20}$=−6.0; (c=3.91; $CHCl_3$)

$C_{20}H_{44}O_4Si_2$: EA: Cld.: C, 59.4%; H, 11.0% (M=404.73 g.mol$^{-1}$) Fnd.: C, 59.50%; H, 10.74%

Example P (5S)-4,6-Bis-[(1,1-dimethylethyl)dimethylsilyloxy]-3,3-dimethyl-hexan-2-one 5.5 ml of a 1M trimethylsilylmethyllithium solution in pentane (2.2 equivalents) is added in a portion at 0° C. to a solution of (1.013 g, 2.5 mmol) of the compound, produced according to Example O, in absolute pentane (12 ml). After 4 hours of stirring, 2.5 ml of MeOH is added to the colorless suspension, and the resulting pale yellow emulsion is stirred vigorously for 1 hour at room temperature.

For working-up, it is diluted with diethyl ether/water, the phases are then separated, and the aqueous phase is extracted three more times with diethyl ether. The combined organic phases are dried on $NaSO_4$, filtered and concentrated by evaporation. Flash chromatography on silica gel (75 g, hex/$Et_2O$, 98:2) produced 947 mg (97%) of the title compound as a colorless oil.

$R_f$-value (hex/EE=96:4)≈0.4 F III (yellow-brown);

$^1$H-NMR (400 MHz, $CDCl_3$): δ in ppm=−0.01 (s, 3H, —$SiCH_3$); 0.00 (s, 3H, —$SiCH_3$); 0.02 (s, 3H, —$SiCH_3$); 0.06 (s, 3H, —$SiCH_3$); 0.85 (s, 18H, —SiC($CH_3$)$_3$); 1.01 (s, 3H, 3-$CH_3$); 1.06 (s, 3H, 3-$CH_3$); 1.39–1.59 (m, 2H, 5-H); 2.10 (s, 3H, 1-H); 3.54–3.64 (m, 2H, 6-H); 4.00 (dd, $J_{4-H,5a-H}$=3.0 Hz, $J_{4-H,5b-H}$=8.0 Hz, 1H, 3-H).

$^{13}$C-NMR (100 MHz, $CDCl_3$): δ in ppm=−4.9 ($SiCH_3$); −3.7 ($SiCH_3$); −3.6 ($SiCH_3$); 18.6 (SiC($CH_3$)$_3$); 18.7 (SiC($CH_3$)$_3$); 20.4 (3-$CH_3$); 22.3 (3-$CH_3$); 26.3 (SiC($CH_3$)$_3$); 26.4 (SiC($CH_3$)$_3$); 27.1 (C-1); 37.6 (C-5); 53.8 (C-3); 60.4 (C-1); 73.7 (C-6); 213.7 (C-2).

MS (Fl, 7 kV, 3 mA, ° C.): m/e=389 ([M+H], 1); 331 ([M−tBu], 100).

Example Q (3S)-1,3-[(1,1-Dimethylethyl)dimethylsilyloxy]-4,4-dimethyl-pentan-5-ol In 100 ml of absolute toluene, 4.047 g (10 mmol) of the compound, produced according to Example P, is mixed drop by drop at −20° C. with 30 ml (3 equivalents) of a 1M DIBAH solution (in heptane) and stirred for 2 more hours.

It is now quenched at 0° C. by adding 5 ml of MeOH, diluted with 150 ml of ether and slowly mixed with 250 ml of saturated NaK-tartrate solution, and vigorous stirring is continued until two clear phases have formed. The phases are separated, the aqueous phase is extracted three more times with ether, the combined organic phases are then dried on $MgSO_4$, filtered on 1 cm of silica gel and concentrated by evaporation.

Chromatographic purification on a 10:1-hex/EE-silica gel column produced 3.527 g (93.6%) of the title compound as a colorless oil.

$R_f$-value (hex/EE 10:1)≈0.32

$R_f$-value (hex/EE=5:1)≈0.53 F I (intense blue);

$^1$H NMR (400 MHz, CDCl$_3$): δ in ppm=0.04 (s, 6H, —Si(CH$_3$)$_2$); 0.078 (s, 3H, —SiCH$_3$); 0.084 (s, 3H, —SiCH$_3$); 0.79 (s, 3H, 2-CH$_3$); 0.878 (s, 9H, —SiC(CH$_3$)$_3$); 0.883 (s, 9H, —SiC(CH$_3$)$_3$); 0.98 (s, 3H, 2-CH$_3$); 1.62 (m, 1H, 4-H); 1.90 (m, 1H, 4-H); 2.87 (dd, J=7.0 Hz, J=4.0 Hz, 1H, 1-OH); 3.28 (dd, J=10.5 Hz, J=7.0 Hz, 1H, 3-H); 3.66 (m, 4H, 1-H and 5-H).

$^{13}$C-NMR (100 MHz, CDCl$_3$): δ in ppm=−5.33 (SiCH$_3$); −5.30 (SiCH$_3$); −4.3 (SiCH$_3$); −4.0 (SiCH$_3$); 18.2 (SiC(CH$_3$)$_3$); 18.3 (SiC(CH$_3$)$_3$); 22.0 (2-CH$_3$); 22.8 (2-CH$_3$); 25.9 (SiC(CH$_3$)$_3$); 26.0 (SiC(CH$_3$)$_3$); 36.4 (C-2); 39.3 (C-4); 60.7 (C-5); 70.2 (C-1); 76.7 (C-3).

IR (Si film): ν in cm$^{-1}$=3450br; 2958s; 2931s; 2885m; 2858s; 1473m; 1464m; 1407w; 1389m; 1361m; 1256s; 1103vs; 1043s; 1006m; 939m; 836vs.

MS (EI, eV, °C.): m/e=377 ([M], 3); 350; 321 (10); 320 (25); 319 ([M−tBu], 100); 261; 187; 173 (1); 131; 115 (4); 114.

C$_{19}$H$_{44}$O$_3$Si$_2$: EA: Cld.: C, 60.6%; H, 11.8% (M=376.72 g.mol$^{-1}$) Fnd.: C, 60.82%; H, 11.70%

Example R (3S)-3,5-[(1,1-Dimethylethyl)dimethylsilyloxy]-2,2-dimethyl-pentanal

In 100 ml of absolute CH$_2$Cl$_2$ and 2 ml of absolute pyridine, 820 mg (2.177 mmol) of the compound, produced according to Example Q, is mixed in portions at 0° C. with 1.21 g (1.3 equivalents, 2.83 mmol) of Dess-Martin-periodinane and stirred for 2 more hours. It is now diluted with 100 ml of ether (formation of precipitate), filtered, and the filtrate is washed twice with 50 ml each of saturated NaHCO$_3$/saturated Na$_2$S$_2$O$_3$ solution (1:1). The phases are separated, the aqueous phase is extracted twice more with CH$_2$Cl$_2$, the combined organic phases are dried on MgSO$_4$, filtered on 1 cm of silica gel and concentrated by evaporation. The crude aldehyde is immediately used after drying by the oil pump (about 0.1 mbar).

$R_f$-value (hex/EE=10:1)≈0.67 F I (blue);

Example S (3S,5RS)-1,3-Bis[(1,1-dimethylethyl)dimethylsilyloxy]-4,4-dimethyl-heptan-5-ol The compound that is produced according to Example R is mixed in 10 ml of absolute diethyl ether at 0° C. drop by drop with 762 μl (≧1.05 equivalents, 2.286 mmol) of a 3M EtMgBr solution (in ether). After 2 hours, it is diluted with ether and quenched by adding 50 ml of saturated NH$_4$Cl solution. The phases are separated, the aqueous phase is extracted three more times with ether, the combined organic phases are then dried on MgSO$_4$, filtered and concentrated by evaporation.

Chromatographic purification on a 25:1-hex/EE-silica gel column produced 530 mg (60.2%) of the title compound and 316 mg (38.5%) as a by-product (Example Q), resulting from the reduction by the EtMgBr.

$R_f$-value (hex/EE=10:1) of nonpolar product≈0.53

$R_f$-value (hex/EE=10:1) of polar product≈0.44

$R_f$-value (hex/ether=9:1) of nonpolar product≈0.32

$R_f$-value (hex/ether=9:1) of polar product≈0.25 F I (blue);

$^1$H-NMR (400 MHz, CDCl$_3$) of nonpolar product: δ in ppm=0.03 (s, 3H, —SiCH$_3$); 0.04 (s, 3H, —SiCH$_3$); 0.11 (s, 3H, —SiCH$_3$); 0.112 (s, 3H, —SiCH$_3$); 0.73 (s, 3H, 4-CH$_3$); 0.88 (s, 9H, —SiC(CH$_3$)$_3$); 0.90 (s, 9H, —SiC(CH$_3$)$_3$); 0.97 (s, 3H, 4-CH$_3$); 1.00 (t, J=7.0 Hz, 3H, 7-H); 1.35 (m, 2H, 6-H); 1.70 (mc, 1H, 2-H); 1.92 (mc, 1H, 2-H); 3.63 (m, 2H, 1-H); 3.71 (m, 1H, 3-H); 4.29 (s, 1H, 5-OH).

$^{13}$C-NMR (100 MHz, CDCl$_3$) of nonpolar product: δ in ppm=−5.31 (SiCH$_3$); −5.27 (SiCH$_3$); −4.3 (SiCH$_3$); −3.9 (SiCH$_3$); 11.3 (C-7); 18.20 (SiC(CH$_3$)$_3$); 18.24 (SiC(CH$_3$)$_3$); 20.5 (4-CH$_3$); 23.5 (4-CH$_3$); 24.5 (C-6); 25.9 (SiC(CH$_3$)$_3$); 26.1 (SiC(CH$_3$)$_3$); 36.0 (C-2); 40.7 (C-4); 60.1 (C-1); 77.4 (C-3); 80.5 (C-5).

IR (Si film): ν in cm$^{-1}$=3500br; 2957vs; 2930s; 2884s; 2858s; 1472s; 1464m; 1409w; 1389m; 1362m; 1326w; 1256s; 1216w; 1101vs; 1048m; 1022m; 1004s; 976w; 955m; 940m; 925w; 836vs; 810m; 776s.

MS (Fl, 7 kV, 3 mA, 20° C.): m/e=405 ([M], 4); 349 (7); 348 (27); 347 ([M−tBu], 100); 159 (3); 115 (7).

C$_{21}$H$_{48}$O$_3$Si$_2$: EA: Cld.: C, 62.3%; H, 12.0% (M=404.76 g.mol$^{-1}$) Fnd.: C, 62.57%; H, 11.98%

$^1$H-NMR (400 MHz, CDCl$_3$) of polar product: δ in ppm=0.05 (s, 3H, —SiCH$_3$); 0.06 (s, 3H, —SiCH$_3$); 0.07 (s, 6H, —Si(CH$_3$)$_2$); 0.74 (s, 3H, 4-CH$_3$); 0.85 (s, 3H, 4-CH$_3$); 0.89 (s, 9H, —SiC(CH$_3$)$_3$); 0.90 (s, 9H, —SiC(CH$_3$)$_3$); 0.98 (t, J=7.0 Hz, 3H, 7-H); 1.29 (mc, 1H, 6-H); 1.49 (m, 2H, 2-H); 2.00 (mc, 1H, 6-H); 2.74 (dd, J=4.5 Hz, J=1.0 Hz, 1H, 5-OH); 3.33 (ddd, J=10.0 Hz, J=4.5 Hz, J=1.5 Hz, 1H, 3-H); 3.68 (td, J=9.5 Hz, J=4.5 Hz, 1H, 5-H); 3.75 (m, 2H, 1-H).

$^{13}$-NMR (100 MHz, CDCl$_3$) of polar product: δ in ppm=−5.4 (2-SiCH$_3$); −4.4 (SiCH$_3$); −3.6 (SiCH$_3$); 11.7 (C-7); 18.3 (SiC(CH$_3$)$_3$); 18.4 (SiC(CH$_3$)$_3$); 18.5 (4-CH$_3$); 18.7 (4-CH$_3$); 24 .2 (C-6); 26.0 (SiC(CH$_3$)$_3$); 26.1 (SiC(CH$_3$)$_3$); 36.5 (C-2); 42.8 (C-4); 61.9 (C-1); 75.5 (C-3); 78.0 (C-5).

IR (Si film): ν in cm$^{-1}$=3484br; 2957vs; 2931s; 2884m; 2858m; 1472m; 1464m; 1389w; 1361w; 1256s; 1094vs; 1034w; 1005w; 938m; 836vs; 775s.

MS (Fl, 7 kV, 3 mA, 20° C.): m/e=405 ([M], 7); 365 (2); 364 (8); 349 (7); 348 (26); 347 ([M−tBu], 100); 307 (6); 306 (17); 305 (78); 267 (3); 115 (3).

C$_{21}$H$_{48}$O$_3$Si$_2$: (M=404.76 g.mol$^{-1}$)

Example T (5S)-5,7-Bis[(1,1-dimethylethyl)dimethylsilyloxy]-4,4-dimethyl-heptan-3-one (Compound of Formula 2)

1.) Variant

In 60 ml of absolute CH$_2$Cl$_2$ and 1 ml of absolute pyridine, 495 mg (1.223 mmol) of the compound that is produced according to Example S is mixed in portions at 0° C. with 778 mg (1.5 equivalents, 1.834 mmol) of Dess-Martin-periodinane, and it is stirred for 2 more hours. It is now diluted with 100 ml of ether (formation of precipitate), filtered, and the filtrate is washed twice with 60 ml each of saturated NaHCO$_3$/saturated Na$_2$S$_2$O$_3$ solution (1:1). The phases are separated, the aqueous phase is extracted twice more with CH$_2$Cl$_2$, the combined organic phases are dried on MgSO$_4$, filtered on 1 cm of silica gel and concentrated by evaporation. After drying by the oil pump (about 0.1 mbar), 487 mg (99%) of the title compound was obtained as (NMR-clean) colorless oil.

2.) Variant n-BuLi (0.3 ml, 2.5 M solution in hexane, 0.75 mmol, 1.33 equivalents) is added in drops at −78° C. to a solution of DIPA (110 μl, 0.78 mmol, 1.38 equivalents) in absolute THF (4 ml), and it is allowed to heat slowly (40 minutes) to room temperature.

A solution of (220 mg, 0.566 mmol) of the compound, produced according to Example P, in absolute THF is quickly added in drops to the LDA solution that is again cooled to −78° C. After 30 minutes of stirring, methyl iodide (0.5 ml, 9 mmol, 16 equivalents) is added to the enolate solution, the cooling bath is removed, and it is stirred for 1.5 more hours.

For working-up, it is quenched at 0° C. with 10 ml of saturated $NH_4Cl$ solution, the phases are separated, the aqueous phase is shaken out three more times with 10 ml of $CH_2Cl_2$ each. The combined organic phases are dried on $NaSO_4$, filtered and concentrated by evaporation. Flash chromatography on silica gel (10 g, hex/$Et_2O$, 97:3) produced 195 mg (85%) of the title compound as a colorless oil.

$R_f$-value (MC/hex=1:1)≈0.44 F I (blue); F III (intense violet-blue);

$^1$H-NMR (400 MHz, $CDCl_3$): δ in ppm=0.02 (s, 3H, —$SiCH_3$); 0.03 (s, 3H, —$SiCH_3$); 0.04 (s, 3H, —$SiCH_3$); 0.08 (s, 3H, —$SiCH_3$); 0.87 (s, 9H, —$SiC(CH_3)_3$); 0.88 (s, 9H, —$SiC(CH_3)_3$); 0.99 (t, J=7.3 Hz, 3H, 7-$CH_3$); 1.04 (s, 3H, 4-$OH_3$); 1.10 (s, 3H, 4-$CH_3$); 1.50 (m, 2H, 2-H); 2.51 (dq, 2H, 6-H each); 3.62 (m, 2H, 1-H); 4.06 (dd, J=7.5 Hz, J=3.0 Hz, 1H, 3-H).

$^{13}$C-NMR (100 MHz, $CDCl_3$): δ in ppm=−5.3 (2-$SiCH_3$); −4.1 (2-$SiCH_3$); 7.7 (C-7); 18.3 (2-$SiC(CH_3)_3$); 20.0 (4-$CH_3$); 22.2 (4-$CH_3$); 25.9 ($SiC(CH_3)_3$); 26.1 ($SiC(CH_3)_3$); 31.6 (C-6); 37.3 (C-2); 53.0 (C-4); 60.1 (C-1); 73.4 (C-3); 215.6 (C=0).

IR (Si film): ν in cm$^{-1}$=2956s; 2928s; 2895m; 2856s; 1472m; 1462m; 1388w; 1360w; 1255m; 1183w; 1097vs; 1006w; 940m; 836vs; 775s.

MS (Fl, 7 kV, 3 mA, 20° C.): m/e=403 ([M]); 347; 346 ([M−tBu]); 345 (100); 303; 57.

$C_{21}H_{46}O_3Si_2$: EA: Cld.: C, 62.6%; H, 11.5% (M=402.76 g.mol$^{-1}$) Fnd.: C, 62.67%; H, 11.29%

EXAMPLES U–V

Production of Compound 234

Example U (2S,6Z,9S,10E)-9-[(1,1-Dimethylethyl) dimethylsilyloxy]-11-(2-methylthiazol-4-yl)-2,6,10-trimethyl-undeca-6,10-dien-1-ol In 80 ml of MeOH/$CH_2Cl_2$ (1:1), 1.385 g (2.509 mmol) of the compound that is produced according to Example L is mixed in portions at 0° C. with 583 mg (1 equivalent, 2.509 mmol) of CSA, and it is stirred for 5 more hours, whereby the temperature may slowly rise to 10° C.

The reaction is quenched by the addition of 150 ml of saturated $NaHCO_3$ solution and diluted with 150 ml of ether. The phases are separated, the aqueous phase is extracted twice more with 100 ml of ether each, the combined organic phases are then dried on $MgSO_4$, filtered on 2 cm of silica gel and concentrated by evaporation in a vacuum.

Chromatographic purification on a 5:1-hex/EE-silica gel column produced 1.094 g (99.6%) of the title compound as a colorless, viscous oil.

$R_f$-value (hex/EE=5:1)≈0.11

$^1$H-NMR (400 MHz, $CDCl_3$): δ in ppm=−0.01 (s, 3H, —$SiCH_3$); 0.03 (s, 3H, —$SiCH_3$); 0.88 (s, 9H, —$SiC(CH_3)_3$); 0.90 (d, J=6.5 Hz, 3H, 2-$CH_3$); 1.32–1.42 (m, 3H); 1.60 (m, 1H, 2-H); 1.66 (d, $^4$J=1.0 Hz, 3H, 6-$CH_3$); 1.96 (m, 1-2H); 1.98 (d, $^4$J=1.0 Hz, 3H, 10-$CH_3$); 2.24 (m, 2H, 8-H); 2.69 (s, 3H, TAr—$CH_3$); 3.39 (m, 1H, 1-H); 3.43 (m, 1H, 1-H); 4.08 (dd, $J_{9\text{-}H,8\text{-}H}$=$J_{9\text{-}H,8'\text{-}H}$=6.5 Hz, 1H, 9-H); 5.14 (dd, $J_{7\text{-}H,8\text{-}H}$=$J_{7\text{-}H,8'H}$=7.0 Hz, 1H, 7-H); 6.44 (s, 1H, 11-H); 6.91 (s, 1H, TAr—$CH_{arom}$).

$^{13}$C-NMR (100 MHz, $CDCl_3$): δ in ppm=−4.9 ($SiCH_3$); −4.7 ($SiCH_3$); 13.9 (10-$CH_3$); 16.2 (2-$CH_3$); 18.2 ($SiC(CH_3)_3$); 19.1 (TAr—$CH_3$); 23.4 (6-$CH_3$); 25.3 (C-5); 25.8 ($SiC(CH_3)_3$); 32.1 (C-4); 33.1 (C-3); 35.5 (C-8); 35.7 (C-2); 68.1 (C-1); 79.2 (C-9); 114.8 (C-13); 118.7 (C-11); 121.7 (C-7); 136.8 (C-6); 142.7 (C-10); 153.2 (C-12); 164.4 (C-14).

IR (Si film): ν in cm$^{-1}$=3385br; 2956s; 2927s; 2856s; 1508w; 1461m; 1449m; 1406w; 1388w; 1376w; 1360w; 1253m; 1184m; 1102vs; 1005m; 940s; 888s; 836vs; 776s; 737m.

MS (Fl, 7 kV, 3 mA, 150° C.): m/e=439 ([M+H]); 438 ([M]); 396; 380; 284; 283; 282 (100); 183; 143; 115; 57.

Angle of rotation: $[α]_D^{20}$=+9.5; (c=1.37; $CHCl_3$)

$C_{24}H_{43}NO_2SSi$: (M=437.75 g.mol$^{-1}$)

Example V (3S,6R,7S,8S,12Z,15S,16E)-4,4,6,8,12,16-Hexamethyl-7-hydroxy-16-(2-methylthiazol-4-yl)-1,3,15-tris[(1,1-dimethylethyl)dimethylsilyloxy]-hepta-dec-12,16-dien-5-one (Compound of Formula 234, whereby R=methyl)

In 80 ml of absolute $CH_2Cl_2$ with 2 ml of absolute pyridine, 983 mg (2.246 mmol) of the compound, produced according to Example U, is mixed in portions at 0° C. with 1.24 g (1.3 equivalents, 2.92 mmol) of Dess-Martin-periodinane and stirred for 4 more hours. For working-up, it is diluted with 200 ml of ether (formation of precipitate), filtered on a 1 cm silica gel frit, and then the filtrate is washed three times with 100 ml each of saturated $NaHCO_3$/saturated $Na_2S_2O_3$ solution (1:1). The organic phase is dried on $MgSO_4$, filtered on 5 cm of silica gel and concentrated by evaporation. The crude aldehyde is then dried in an oil pump vacuum (about 0.1 mbar) and thus immediately used in the subsequent reaction.

In 10 ml of absolute THF, 441 μl (1.4 equivalents, 3.14 mmol) of DIPA is slowly mixed at −20° C. with 1.258 ml (1.4 equivalents, 3.14 mmol) of a 2.5 M nBuLi solution (in hexane) and stirred for 20 more minutes. The finished LDA solution is cooled to −78° C., mixed slowly with 1.266 g (1.4 equivalents, 3.14 mmol) of the compound that is produced according to Example T and diluted in 10 ml of absolute THF, stirred for 15 more minutes and allowed to heat to −35° C. over a period of 45 minutes. Then, it is cooled to −95° C., added drop by drop to the crude aldehyde, dissolved in some absolute THF, and stirred for 90 more minutes, whereby the temperature may rise slowly to −80° C. For working-up, the cooling bath is removed, quenched with 50 ml of saturated $NH_4Cl$ solution and diluted with ether. The phases are separated, the aqueous phase is extracted twice more with ether, the combined organic phases are dried on $MgSO_4$, filtered and concentrated by evaporation.

Chromatographic precleaning on 25:1-hex/EE-silica gel columns produced 1.305 g (69%, over two stages) of the title compound as a mixed fraction of the two diastereomers. The separation of the diastereomeric aldol products was carried out via preparative HPLC in 9:1-hex/EE.

$R_f$-value (MC) of aldehyde≈0.26

$R_f$-value (MC) of the title compound≈0.14

$^1$H-NMR (400 MHz, $CDCl_3$) of aldehyde: δ in ppm=−0.01 (s, 3H, —$SiCH_3$); 0.03 (s, 3H, —$SiCH_3$); 0.88 (s, 9H, —$SiC(CH_3)_3$); 1.07 (d, J=6.5 Hz, 3H, 2-$CH_3$); 1.30–1.43 (m, 3H); 1.65 (d, $^4$J=1.5 Hz, 3H, 6-$CH_3$); 1.64–1.72 (m, 1H); 1.99 (d, $^4$J=1.0 Hz, 3H, 10-$CH_3$); 2.00–2.06 (m, 2H);

2.18–2.33 (m, 3H); 2.69 (s, 3H, TAr—CH$_3$); 4.07 (t, J$_{9-H, 8-H}$=J$_{9-H,8'-H}$=6.5 Hz, 1H, 9-H); 5.15 (, J$_{7-H,8-H}$=J$_{7-H,8'-H}$=6.5 Hz, 1H, 7-H); 6.44 (s, 1H, 11-H); 6.91 (s, 1H, TAr—CH$_{arom}$); 9.59 (d, J=1.5 Hz, 1H, 1-H).

$^{13}$C-NMR (100 MHz, CDCl$_3$) of aldehyde: δ in ppm=–5.0 (SiCH$_3$); –4.7 (SiCH$_3$); 13.3 (2-CH$_3$); 14.0 (10-CH$_3$); 18.2 (SiC(CH$_3$)$_3$); 19.2 (TAr—CH$_3$); 23.4 (6-CH$_3$); 25.2 (C-5); 25.8 (SiC(CH$_3$)$_3$); 30.4 (C-4); 31.8 (C-3); 35.4 (C-8); 46.3 (C-2); 78.9 (C-9); 115.0 (C-13); 118.7 (C-11); 122.1 (C-7); 136.0 (C-6); 142.4 (C-10); 153.2 (C-12); 164.3 (C-14); 205.1 (C-1).

$^1$H-NMR (400 MHz, CDCl$_3$) of the title compound: δ in ppm=–0.01 (s, 3H, —SiCH$_3$); 0.02 (s, 6H, —Si(CH$_3$)$_2$); 0.03 (s, 3H, —SiCH$_3$); 0.07 (s, 3H, —SiCH$_3$); 0.09 (s, 3H, —SiCH$_3$); 0.81 (d, J=7.0 Hz, 3H, 8-CH$_3$); 0.87 (s, 18H, —SiC(CH$_3$)$_3$); 0.89 (s, 9H, —SiC(CH$_3$)$_3$); 1.01 (d, J=7.0 Hz, 3H, 6-CH$_3$); 1.08 (s, 3H, 4-CH$_3$); 1.20 (s, 3H, 4-CH$_3$); 1.24–1.35 (m, 2H); 1.43–1.53 (m, 3H); 1.57–1.67 (m, 1H); 1.65 (s, 3H, 12-CH$_3$); 1.69–1.77 (m, 1H); 1.90–2.02 (m, 2H, 11-H); 1.98 (s, 3H, 16-CH$_3$); 2.23 (m, 2H, 14-H); 2.70 (s, 3H, TAr—CH$_3$); 3.29 (m, 1H, 6-H); 3.59 (m, 1H); 3.66 (m, 1H, 7-H); 3.89 (dd, J=7.5 Hz, J=3.0 Hz, 1H, 15-H); 4.08 (t, J=6.5 Hz, 1H, 3-H); 5.12 (t, J=7.6 Hz, 1H, 13-H); 6.44 (s, 1H, 17-H); 6.90 (s, 1H, TAr—CH$_{arom}$).

$^{13}$C-NMR (100 MHz, CDCl$_3$) of the title compound: δ in ppm=–5.3 (SiCH$_3$); –4.9 (SiCH$_3$); –4.7 (SiCH$_3$); –4.1 (SiCH$_3$); –3.8 (SiCH$_3$); 9.6 (6-CH$_3$); 13.9 (16-CH$_3$); 15.4 (8-CH$_3$); 18.3 (SiC(CH$_3$)$_3$); 19.2 (TAr—CH$_3$); 20.5 (4-CH$_3$); 22.9 (4-CH$_3$); 23.5 (12-CH$_3$); 25.2 (C-11); 25.9 (SiC(CH$_3$)$_3$); 26.1 (SiC(CH$_3$)$_3$); 32.4 (C-10); 33.0 (C-9); 35.3 (C-14); 35.5 (C-8); 37.9 (C-2); 41.4 (C-6); 54.0 (C-4); 60.5 (C-1); 74.2+74.9 (C-3 and C-7); 79.1 (C-15); 114.9 (C-19); 118.7 (C-17); 121.5 (C-13); 136.9 (C-12); 142.6 (C-16); 153.3 (C-18); 164.3 (C-20); 222.2 (C-5).

IR (Si film): ν in cm$^{-1}$=2956s; 2932s; 2885s; 2858s; 1472s; 1463s; 1444m; 1389m; 1366m; 1257vs; 1198m; 1132m; 1075m; 1006m; 940w; 874m; 838s; 814m; 777vs.

$^1$H-NMR (400 MHz, CDCl$_3$) of polar product: δ in ppm=–0.01 (s, 3H, —SiCH$_3$); 0.02 (s, 3H, —SiCH$_3$); 0.03 (s, 3H, —SiCH$_3$); 0.04 (s, 3H, —SiCH$_3$); 0.05 (s, 3H, —SiCH$_3$); 0.10 (s, 3H, —SiCH$_3$); 0.87 (s, 9H, —SiC(CH$_3$)$_3$); 0.88 (s, 18H, —SiC(CH$_3$)$_3$); 0.97 (d, J=6.5 Hz, 3H, 8-CH$_3$); 1.05 (d, J=6.5 Hz, 3H, 6-CH$_3$); 1.10 (s, 3H, 4-CH$_3$); 1.14 (s, 3H, 4-CH$_3$); 1.29–1.41 (m, 3H); 1.51 (m, 3H); 1.58 (m, 1H); 1.67 (s, 3H, 12-CH$_3$); 1.90–2.00 (m, 2H, 11-H); 1.99 (d, $^4$J=1.0 Hz, 3H, 16-CH$_3$); 2.18–2.30 (m, 2H, 14-H); 2.70 (s, 3H, TAr—CH$_3$); 3.22 (qd, J=7.0 Hz, J=2.0 Hz, 1H, 6-H); 3.40 (d, J=8.0 Hz, 1H, 7-OH); 3.47 (s, 1H); 3.58–3.69 (m, 2H); 4.03 (dd, J=7.0 Hz, J=3.5 Hz, 1H, 15-H); 4.08 (t, J=7.0 Hz, 1H, 3-H); 5.14 (t, J=7.0 Hz, 1H, 13-H); 6.45 (s, 1H, 17-H); 6.90 (s, 1H, TAr—CH$_{arom}$).

$^{13}$C-NMR (100 MHz, CDCl$_3$) of polar product: δ in ppm=–5.3 (SiCH$_3$); –4.9 (SiCH$_3$); –4.7 (SiCH$_3$); –4.0 (SiCH$_3$); –3.7 (SiCH$_3$); 10.8 (C-6); 13.9 (16-CH$_3$); 15.5 (8-CH$_3$); 18.4 (SiC(CH$_3$)$_3$); 19.2 (TAr—CH$_3$); 19.6 (4-CH$_3$); 22.8 (4-CH$_3$); 23.6 (12-CH$_3$); 25.2 (C-11); 25.8 (SiC(CH$_3$)$_3$); 25.9 (SiC(CH$_3$)$_3$); 26.2 (SiC(CH$_3$)$_3$); 32.3 (C-10); 32.9 (C-9); 35.4 (C-14); 35.5 (C-8); 37.8 (C-2); 41.4 (C-6); 54.3 (C-4); 60.2 (C-1); 72.7+75.1 (C-3 and C-7); 79.0 (C-15); 114.9 (C-19); 118.7 (C-17); 121.7 (C-13); 136.6 (C-12); 142.5 (C-16); 153.2 (C-18); 164.3 (C-20); 221.8 (C-5).

IR (Si film): ν in cm$^{-1}$=2956m; 2928m; 2856m; 1686w; 1619w; 1508w; 1472m; 1462m; 1407w; 1388m; 1361m; 1322w; 1255m; 1183m; 1104vs; 1032m; 977m; 939m; 836s; 775s; 738m.

Example W (3S,6R,7S,8S,12Z,15S,16E)-4,4,6,8,12,16-Hexamethyl-16-(2-methylthiazol-4-yl)-1,3,7,15-tetrakis[(1,1-dimethylethyl)dimethylsilyloxy]-heptadec-12,16-dien-5-one 493 mg (0.588 mmol) of the compound that is produced according to Example V is introduced at 0° C. with 250 μl of 2,6-lutidine (3 equivalents, 1.764 mmol) into 15 ml of absolute CH$_2$Cl$_2$. 203 μl (1.5 equivalents, 0.882 mmol) of TBS triflate is now slowly added in drops.

After 3 hours at 0° C., the cooling bath is removed, and the reaction is quenched by adding saturated NH$_4$Cl solution. The phases are separated, the aqueous phase is extracted twice more with CH$_2$Cl$_2$, the combined organic phases are then dried on MgSO$_4$, filtered on 5 cm of silica gel and concentrated by evaporation.

Chromatographic purification on a 25:1-hex/EE-silica gel column produced 560 mg (quant.) of the title compound as a colorless oil.

R$_f$-value (hex/EE=10:1)≈0.56 F IV (intense blue);

$^1$H-NMR (400 MHz, CDCl$_3$): δ in ppm=–0.01 (s, 3H, —SiCH$_3$); 0.017 (s, 3H, —SiCH$_3$); 0.02 (s, 3H, —SiCH$_3$); 0.03 (s, 3H, —SiCH$_3$); 0.047 (s, 6H, —SiCH$_3$); 0.053 (s, 3H, —SiCH$_3$); 0.08 (s, 3H, —SiCH$_3$); 0.871 (s, 9H, —SiC(CH$_3$)$_3$); 0.876 (s, 9H, —SiC(CH$_3$)$_3$); 0.88 (s, 9H, —SiC(CH$_3$)$_3$); 0.875 (v, 3H, 8-CH$_3$); 0.89 (s, 9H, —SiC(CH$_3$)$_3$); 1.01 (s, 3H, 4-CH$_3$); 1.03 (d, J=7.0 Hz, 3H, 6-CH$_3$); 1.21 (s, 3H, 4-CH$_3$); 1.24–1.28 (m, 2H); 1.30–1.40 (m, 4H); 1.64 (s, 3H, 12-CH$_3$); 1.90–1.97 (m, 2H, 11-H); 1.98 (d, $^4$J=1.0 Hz, 3H, 16-CH$_3$); 2.22 (m, 2H, 14-H); 2.70 (s, 3H, TAr—CH$_3$); 3.13 (qd, J=? Hz, J=6.5 Hz, 1H, 6-H); 3.56 (ddd, J=? Hz, J=7.5 Hz, J=2.0 Hz, 1H, 1-H); 3.66 (td, J=9.6 Hz, J=9.0 Hz, J=5.0 Hz, 1H, 1-H); 3.75 (dd, J=7.0 Hz, J=1.5 Hz, 1H, 7-H); 3.87 (dd, J=7.5 Hz, J=2.5 Hz, 1H, 15-H); 4.07 (t, J=6.5 Hz, 1H, 3-H); 5.12 (t, J=7.0 Hz, 1H, 13-H); 6.44 (s, 1H, 17-H); 6.90 (s, 1H, TAr—CH$_{arom}$).

$^{13}$C-NMR (100 MHz, CDCl$_3$): δ in ppm=–5.3 (SiCH$_3$); –4.9 (SiCH$_3$); –4.7 (SiCH$_3$); –4.0 (SiCH$_3$); –3.8 (SiCH$_3$); –3.7 (SiCH$_3$); 13.9 (16-CH$_3$); 15.4 (8-CH$_3$); 17.5 (6-CH$_3$); 18.2 (SiC(CH$_3$)$_3$); 18.3 (SiC(CH$_3$)$_3$); 18.5 (SiC(CH$_3$)$_3$); 19.2 (TAr—CH$_3$); 19.4 (4-CH$_3$); 23.5 (12-CH$_3$); 24.5 (4-CH$_3$); 24.9 (C-11); 25.9 (SiC(CH$_3$)$_3$); 26.0 (SiC(CH$_3$)$_3$); 26.1 (SiC(CH$_3$)$_3$); 26.2 (SiC(CH$_3$)$_3$); 31.1 (CH$_2$); 32.6 (CH$_2$); 35.3 (C-14); 38.1 (C-2); 39.0 (CH); 45.0 (C-6); 53.7 (C-4); 61.0 (C-1); 74.1 (C-3); 77.5 (C-7); 79.0 (C-15); 114.9 (C-19); 118.7 (C-17); 121.6 (C-13); 136.8 (C-12); 142.5 (C-16); 153.3 (C-18); 218.2 (C-5).

Example X (3S,6R,7S,8S,12Z,15S,16E)-4,4,6,8,12,16-Hexamethyl-16-(2-methylthiazol-4-yl)-3,7,15-tris[(1,1-dimethylethyl)-dimethylsilyloxy]-heptadec-12,16-dien-5-on-1-ol In 20 ml of MeOH/CH$_2$Cl$_2$ (1:1), 540 mg (≈0.567 mmol) of the compound that is produced according to Example W is slowly mixed at 0° C. with 132 mg (1 equivalent, 0.567 mmol) of CSA and stirred for 4 more hours.

For working-up, it is diluted with CH$_2$Cl$_2$, and the reaction is quenched by adding saturated NaHCO$_3$ solution. Then, the phases are separated, the aqueous phase is extracted twice more with CH$_2$Cl$_2$, and the combined organic phases are dried on MgSO$_4$, filtered and spun in.

Flash chromatography on a 10:1-hex/EE-silica gel column produced 412 mg (87%) of the title compound as a colorless oil.

$R_f$-value (hex/EE=10:1)≈0.17 F III (intense blue);

$R_f$-value (hex/EE=5:1)≈0.32 F IV (intense blue);

$^1$H-NMR (400 MHz, CDCl$_3$): δ in ppm=−0.01 (s, 3H, —SiCH$_3$); 0.03 (s, 3H, —SiCH$_3$); 0.06 (s, 9H, 3×-SiCH$_3$); 0.10 (s, 3H, —SiCH$_3$); 0.86–0.92 (m, 30H, 3×—SiC(CH$_3$)$_3$ and 8-CH$_3$); 1.048 (d, J=6.9 Hz, 3H, 6-CH$_3$); 1.051 (s, 3H, 4-CH$_3$); 1.09–1.20 (m, 2H); 1.21 (s, 3H, 4-CH$_3$); 1.26–1.50 (m, 5H); 1.65 (s, 3H, 12-CH$_3$); 1.90–2.05 (m, 2H, 11-H); 1.98 (d, $^4$J=0.9 Hz, 3H, 16-CH$_3$); 2.22 (mc, 2H, 14-H); 2.70 (s, 3H, TAr—CH$_3$); 3.12 (qd, J=7.1 Hz, J=6.7 Hz, 1H, 6-H); 3.63 (dd, J=6.0 Hz, J=5.6 Hz, 2H, 1-H); 3.79 (dd, J=7.1 Hz, J=1.3 Hz, 1H, 7-H), 4.03–4.10 (m, 2H, 3-H and 15-H); 5.13 (t, J=7.5 Hz, 1H, 13-H); 6.44 (s, 1H, 17-H); 6.90 (s, 1H, TAr—CH$_{arom}$).

$^{13}$C-NMR (100 MHz, CDCl$_3$): δ in ppm=−4.9 (SiCH$_3$); −4.7 (SiCH$_3$); −3.93 (SiCH$_3$); −3.91 (SiCH$_3$); −3.8 (SiCH$_3$); −3.6 (SiCH$_3$); 13.9 (16-CH$_3$); 14.2 (6-CH$_3$); 15.6 (8-CH$_3$); 17.6 (4-CH$_3$); 17.8 (4-CH$_3$); 18.2 (SiC(CH$_3$)$_3$); 18.3 (SiC(CH$_3$)$_3$); 18.5 (SiC(CH$_3$)$_3$); 19.2 (TAr—CH$_3$); 23.5 (12-CH$_3$); 24.9 (C-11); 25.9 (SiC(CH$_3$)$_3$); 26.0 (SiC(CH$_3$)$_3$); 26.2 (SiC(CH$_3$)$_3$); 30.9 (C-10); 32.5 (C-9); 35.4 (C-14); 38.4 (C-2); 38.8 (CH); 45.1 (C-6); (C-15); 114.9 (C-19); 118.7 (C-17); 121.6 (C-13); 136.7 (C-12); 142.5 (C-16); 153.3 (C-18); 164.3 (C-20); 218.2 (C-5).

IR (Si film): ν in cm$^{-1}$=3320br; 2956s; 2928s; 1856s; 1686w; 1472m; 1462m; 1407w; 1388m; 1361w; 1255s; 1183w; 1104vs; 1032m; 977m; 939s; 836vs; 775vs; 738s.

MS (Fl, 7 kV, 3 mA, 195° C.): m/e=840 ([M+H]); 839 ([M]); 781; 706; 649; 550; 283; 282 (100); 268; 189; 132; 115; 57.

Example Y (3S,6R,7S,8S,12Z,15S,16E)-4,4,6,8,12,16-Hexamethyl-16-(2-methylthiazol-4-yl)-3,7,15-tris[(1,1-dimethylethyl)dimethylsilyloxy]-heptadec-12,16-dien-5-onic acid In 50 ml of absolute CH$_2$Cl$_2$ and 1 ml of absolute pyridine, 389 mg (0.4639 mmol) of the compound that is produced according to Example X is mixed with 258 mg (1.3 equivalents) of Dess-Martin-periodinane and stirred for 2 more hours. It is now diluted with 150 ml of ether, filtered, and the filtrate is washed with 100 ml of saturated NaHCO$_3$/saturated Na$_2$S$_2$O$_3$ solution (1:1). The phases are separated, the aqueous phase is extracted twice more with CH$_2$Cl$_2$, the combined organic phases are dried on MgSO$_4$, filtered on 1 cm of silica gel, concentrated by evaporation and dried. The crude aldehyde is equally further reacted without being purified, crude, after drying in an oil pump vacuum.

The crude aldehyde is mixed in 10.3 ml of tert-butanol and 10.3 ml of 2,3-dimethyl-but-2-ene at room temperature with a solution of 211 mg (5 equivalents) of NaClO$_2$ and 211 mg of NaH$_2$PO$_4$ in 2.11 ml of water, and it is stirred for 40 more minutes. For working-up, it is diluted with 150 ml (2:1) of CH$_2$Cl$_2$/water, slightly acidified with 2 drops of TFA, the phases are separated, the aqueous phase is extracted twice more with CH$_2$Cl$_2$, the combined organic phases are dried on MgSO$_4$, filtered on 1 cm of silica gel and concentrated by evaporation. Flash chromatography on a 10:1–5:1–3:1-hex/EE-gradient silica gel column produced 380 mg (96.1%) of the title compound as a very viscous, colorless oil.

$R_f$-value (hex/EE=5:1) of the aldehyde≈0.56 F III or F IV (intense blue);

$R_f$-value (hex/EE=5:1) of the title compound≈0.30 F III or F IV (intense violet-blue);

$^1$H-NMR (400 MHz, CDCl$_3$): δ in ppm=−0.02 (s, 3H, —SiCH$_3$); 0.02 (s, 3H, —SiCH$_3$); 0.03 (s, 3H, —SiCH$_3$); 0.07 (s, 3H, —SiCH$_3$); 0.08 (s, 3H, —SiCH$_3$); 0.12 (s, 3H, —SiCH$_3$); 0.88 (s, 18H, —SiC(CH$_3$)$_3$); 0.885 (v, 3H, 8-CH$_3$); 0.89 (s, 9H, —SiC(CH$_3$)$_3$); 1.06 (d, J=7.0 Hz, 3H, 6-CH$_3$); 1.15 (s, 6H, 4-CH$_3$); 1.35–1.50 (m, 5H); 1.67 (s, 3H, 12-CH$_3$); 1.86–1.94 (m, 2H, 11-H); 1.94 (d, $^4$J=1.0 Hz, 3H, 16-CH$_3$); 2.12–2.22 (m, 2 or 3H); 2.33 (dd, J=16.6 Hz, J=6.5 Hz, 1H, 2-H); 2.43 (dd, J=16.6 Hz, J=3.5 Hz, 1H, 2-H); 2.70 (s, 3H, TAr—CH$_3$); 3.13 (qd, J=7.0 Hz, J=6.0 Hz, 1H, 6-H); 3.74 (dd, J=5.5 Hz, J=2.0 Hz, 1H, 7-H); 4.12 (m, 1H, 15-H); 4.40 (dd, J=7.0 Hz, J=3.5 Hz, 1H, 3-H); 5.17 (t, J=7.0 Hz, 1H, 13-H); 6.63 (s, 1H, 17-H); 6.92 (s, 1H, TAr—CH$_{arom}$).

$^{13}$C-NMR (100 MHz, CDCl$_3$): δ in ppm=−5.0 (SiCH$_3$); −4.7 (SiCH$_3$); −4.5 (SiCH$_3$); −4.1 (SiCH$_3$); −4.0 (SiCH$_3$); −3.9 (SiCH$_3$); 14.0 (16-CH$_3$); 15.8 (8-CH$_3$); 16.4 (6-CH$_3$); 18.3 (SiC(CH$_3$)$_3$); 18.5 (SiC(CH$_3$)$_3$); 18.6 (4-CH$_3$); 18.7 (4-CH$_3$); 23.4;−23.5 (12-CH$_3$); 24.9 (C-11); 25.6; 25.8 (SiC(CH$_3$)$_3$); 26.1 (SiC(CH$_3$)$_3$); 26.2 (SiC(CH$_3$)$_3$); 31.7 (C-10); 32.5 (C-9); 33.9 (C-9); 35.4 (C-14); 39.5 (C-8 ?); 39.9; 44.2 (C-6); 54.0 (C-4); 63.7; 73.1 (C-3); 76.7 (C-7); 79.2 (C-15); 114.4 (C-19); 118.1 (C-17); 121.7 (C-13); 137.1 (C-12); 143.7 (C-16); 152.7 (C-18); 165.3 (C-20); 174.0 (C-1); 218.7 (C-5).

MS (Fl, 7 eV, 3 mA, 195° C.): m/e=854 ([M+H]); 853 ([M]); 796; 795; 720; 684; 663; 649; 593; 541; 283; 282; 203; 168; 93; 57.

Example Z (3S,6R,7S,8S,12Z,15S,16E)-3,7-Bis[(1,1-dimethylethyl)dimethylsilyloxy]-4,4,6,8,12,16-hexamethyl-15-hydroxy-16-(2-methylthiazol-4-yl)-heptadeca-12,16-dien-5-onic acid In 10 ml of absolute THF, 365 mg (0.44576 mmol) of the compound that is produced according to Example Y is mixed at room temperature with 2.23 ml (5 equivalents) of a 1 M TBAF solution (in THF) and stirred for 10 more hours.

For working-up, it is diluted with 100 ml of ether and quenched by adding 70 ml of saturated NH$_4$Cl solution. The phases are separated, the aqueous phase is extracted twice more with ether, the combined organic phases are dried on MGSO$_4$, filtered and concentrated by evaporation.

Flash chromatography on a 6:5:1–4:3:1–2:1:1-MC/hex/EE-gradient-silica-gel-column produced 180 mg of the title compound as a colorless, viscous oil.

$^1$H-NMR (400 MHz, CDCl$_3$): δ in ppm=0.04 (s, 3H, —SiCH$_3$); 0.055 (s, 3H, —SiCH$_3$); 0.07 (s, 3H, —SiCH$_3$); 0.10 (s, 3H, —SiCH$_3$); 0.865 (s, 9H, —(SiC(CH$_3$)$_3$); 0.89 (s, 9H, —SiC(CH$_3$)$_3$); 0.90 (d (hv), J≈7.0 Hz, 3H, 8-CH$_3$); 1.05 (d, J=6.5 Hz, 3H, 6-CH$_3$); 1.10 (s, 3H, 4-CH$_3$); 1.19 (s, 3H, 4-CH$_3$); 1.34–1.50 (m, 2H); 1.48–1.56 (mc, 3H); 1.70 (s, 3H, 12-CH$_3$); 1.92–2.01 (m, 1H, 14-H); 2.01 (d, $^4$J=1.0 Hz, 3H, 16-CH$_3$); 2.04–2.14 (m, 1H, 14-H); 2.26 (dd, J=16.6 Hz, J=6.0 Hz, 1H, 2-H); 2.33 (mc, 2H, 11-H); 2.435 (dd, J=16.6 Hz, J=4.0 Hz, 1H, 2-H); 2.70 (s, 3H, TAr—CH$_3$); 3.14 (qd, J=7.0 Hz, J=6.5 Hz, 1H, 6-H); 3.76 (dd, J=7.0 Hz, J=2.0 Hz, 1H, 7-H); 4.14 (t, J=6.5 Hz, 1H, 15-H); 4.40 (dd, J=6.0 Hz, J=4.0 Hz, 1H, 3-H); 5.17 (t, J=7.0 Hz, 1H, 13-H); 6.63 (s, 1H, 17-H); 6.94 (s, 1H, TAr—CH$_{arom}$).

$^{13}$C-NMR (100 MHz, CDCl$_3$): δ in ppm=−4.7 (SiCH$_3$); −4.1 (SiCH$_3$); −3.9 (SiCH$_3$); −3.8 (SiCH$_3$); 13.8 (16-CH$_3$); 14.6 (8-CH$_3$); 16.0 (6-CH$_3$); 17.1; 18.2 (SiC(CH$_3$)$_3$); 18.5 (SiC(CH$_3$)$_3$); 18.9 (TAr—CH$_3$); 19.9 (4-CH$_3$); 23.1

(4-$CH_3$); 23.6 (12-$CH_3$); 26.1 (Si$C(CH_3)_3$); 26.2 (Si$C(CH_3)_3$); 26.3 ($CH_2$); 26.4 ($CH_2$); 31.3 ($CH_2$); 32.5 ($CH_2$); 34.2 ($CH_2$); 39.2 (CH); 40.9 ($CH_2$); 44.8 (CH); 51.9; 53.8 (C-4); 74.2 (C-3); 77.3 (C-7); 77.4 (C-15); 115.1 (C-19); 118.7 (C-17); 120.3 (C-13); 139.4 (C-12); 142.2 (C-16); 152.7 (C-18); 165.0 (C-20); 174.9 (C-1); 217.9 (C-5).

IR (Si film): ν in $cm^{-1}$=3357br; 2958s; 2932s; 2856m; 1696m; 1508w; 1472m; 1387m; 1293m; 1255m; 1186m; 1106vs; 988s; 952m; 875s; 837vs; 815m; 776vs; 737s.

MS (Fl, 7 eV, 3 mA, 190° C.): m/e=739 ([M+H]); 738 ([M]); 722; 721; 720; 682; 662; 606; 427; 329; 295; 203; 129; 57.

Example AA

Silylated Epothilone D 65 mg (0.338 mmol, 2 equivalents) of N'-(3-dimethylaminopropyl)-N-ethylcarbodiimide-HCl (EDCl), 54 mg (0.507 mmol, 3 equivalents) of DMAP and 54 mg (0.338 mmol, 2 equivalents) of DMAP-HCl in 100 ml of ethanol-free absolute $CHCl_3$ [filtered on bas. Alox B and distilled over $CaH_2$] are introduced into a 250 ml three-necked round-bottom flask with an argon connection, pressure equalization and jacketed coil condenser. The solution is heated to reflux temperature, and then a solution of 125 mg (0.169 mmol) of the compound that is produced according to Example Z in 8 ml of absolute $CHCl_3$ is added drop by drop via an injection device over a period of 17 hours and stirred for 30 more minutes after the last addition.

The reaction solution is allowed to cool and quenched by adding 100 ml of saturated $NH_4Cl$ solution and stirred vigorously for 30 more minutes. Then, the phases are separated, the aqueous phase is extracted twice with $CH_2Cl_2$, the combined organic phases are dried on $MgSO_4$, filtered on 0.5 cm of silica gel and concentrated by evaporation.

Chromatography on a 25:1-hex/EE-gradient-silica-gel-column produced 84 mg (69%) of the title compound as a flat yellowish oil.

$R_f$-value (hex/EE=10:1)≈0.37 F III and F IV (violet blue);

$^1$H-NMR (400 MHz, $CDCl_3$): δ in ppm=-0.12 (s, 3H, —$SiCH_3$); 0.07 (s, 3H, —$SiCH_3$); 0.095 (s, 3H, —$SiCH_3$); 0.10 (s, 3H, —$SiCH_3$); 0.83 (s, 9H, —Si$C(CH_3)_3$); 0.93 (s, 9H, —Si$C(CH_3)_3$); 0.97 (d, J=7.0 Hz, 3H, 8-$CH_3$); 1.09 (d, J=6.5 Hz, 3H, 6-$CH_3$); 1.13 (s, 3H, 4-$CH_3$); 1.18 (s, 3H, 4-$CH_3$); 1.47–1.61 (m, 3H); 1.66 (s, 3H, 12-$CH_3$); 1.66–1.77 (m, 2H); 2.02–2.08 (m, 1H or 2H); 2.09 (d, $^4$J=1.0 Hz, 3H, 16-$CH_3$); 2.41–2.49 (m, 1H); 2.62–2.71 (m, 2H); 2.69 (s, 3H, TAr—$CH_3$); 2.79 (dd, J=16.6 Hz, J=1.5 Hz, 1H, 2-H); 3.01 (qd, J=7.0 Hz, J=6.5 Hz, 1H, 6-H); 3.88 (d, J=9.0 Hz, 1H, 7-H); 4.02 (d, J=8.5 Hz, 1H, 3-H); 4.96 (d, J=9.6 Hz, 1H, 15-H); 5.15 (t, J≈8.0 Hz, 1H, 13-H); 6.55 (s, 1H, 17-H); 6.95 (s, 1H, TAr—$CH_{arom}$).

$^{13}$C-NMR (100 MHz, $CDCl_3$): δ in ppm=-5.6 ($SiCH_3$); -3.70 ($SiCH_3$); -3.69 ($SiCH_3$); -3.3 ($SiCH_3$); 15.3+17.8 (C-16 and C-6); 18.6 (Si$C(CH_3)_3$); 18.7 (Si$C(CH_3)_3$); 19.2 (TAr—$CH_3$); 23.1 (4-$CH_3$'s); 24.3; 24.5; 25.7; 26.2 (Si$C(CH_3)_3$); 26.4 (Si$C(CH_3)_3$); 27.4; 29.7; 31.4; 31.9; 32.5; 39.2 (C-2); 53.4 (C-4); 76.3 (C-3 and/or C-7); 79.9 (C-15); 115.9 (C-19); 119.2 (C-17); 119.4 (C-13); 138.8 (C-12); 140.6 (C-16); 152.5 (C-18); 164.5 (C-20); 171.2 (C-1); 215.1 (C-5).

$C_{39}H_{69}NO_5SSi_2$: (M=720.21 g.$mol^{-1}$)

Example AB

Epothilone D 75 mg (0.104 mmol) of the compound that is produced according to Example AA is introduced at 0° C. with 1.5 ml of absolute pyridine into 5 ml of absolute THF. 1.5 ml of HF-pyridine is now added drop by drop and allowed to heat slowly to room temperature. After 18 hours (almost only educt), another 1.5 ml of HF-pyridine is added drop by drop, again at 0° C., and stirred for 18 more hours.

For working-up, it is mixed drop by drop with saturated $NaHCO_3$ solution at 0° C., then diluted with diethyl ether and saturated $NaHCO_3$ solution. Then, the phases are separated, the aqueous phase is extracted three times with diethyl ether, the combined organic phases are dried on $MgSO_4$, filtered and concentrated by evaporation.

Chromatography on a 3:1-hex/EE-silica gel column produced 44 mg (69.8%) (monodesilylated product) and 10 mg (19.6%) of the title compound (epothilone D). The monodesilylated product is again subjected to the above conditions. After chromatography on a 3:1-hex/EE-silica gel column, 39 mg (76.3%) of the title compound was again obtained, thus a total of 49 mg (95.8%) of epothilone D.

$R_f$-value (hex/EE=1.1) monosilylated≈0.67 F IV (blue);

$R_f$-value (hex/EE=3:1) monosilylated≈0.19 F IV (blue);

$R_f$-value (hex/EE=1:1) of the title compound≈0.52 F IV (blue);

$R_f$-value (hex/EE=3:1) of the title compound≈0.11 F IV (blue);

$^1$H-NMR (400 MHZ, $CDCl_3$): δ in ppm=1.01 (d, J=7.0 Hz, 3H, 8-$CH_3$); 1.06 (s, 3H, 4-$CH_3$); 1.18 (d, J=7.0 Hz, 3H, 6-$CH_3$); 1.24–1.31 (m, 4H); 1.33 (s, 3H, 4-$CH_3$); 1.65 (s, 3H, 12-$CH_3$); 1.68–1.78 (m, 1 or 2H, ?); 1.83–1.89 (m, 1H); 2.06 (d, $^4$J=1.0 Hz, 3H, 16-$CH_3$); 2.22 (ddd, J=15.6 Hz, $J_{11-Ha, 10-Ha}$=3.5 Hz, $J_{11-Ha,10-Hb}$=2.0 Hz, 1H, 11-Ha); 2.28 (dd, J=14.6 Hz, $J_{2-Ha,3-H}$=3.0 Hz, 1H, 2-Ha); 2.29–2.35 (m, 1H); 2.45 (dd, $J_{2-Hb,3-H}$=14.6 Hz, $J_{2-Hb,3-H}$=11.0 Hz, 1H, 2-Hb); 2.63 (dt, J=15.1 Hz, $J_{14-Ha,15\ and\ 13-H}$=10.0 Hz, 1H, 14-Ha); 2.68 (s, 3H, TAr—$CH_3$); 3.02 (br, 1H, OH); 3.15 (qd, $J_{6-H,6-CH3}$=6.9 Hz, $J_{6-H,7-H}$=2.5 Hz, 1H, 6-H); 3.45 (br, 1H, OH); 3.71 (dd, $J_{7-H,8-H}$=4.0 Hz, $J_{7-H,6-H}$=2.5 Hz, 1H, 7-H); 4.28 (dd, $J_{3-H,2-Hb}$=11.0 Hz, $J_{3-H,2-Ha}$=2.5 Hz, 1H, 3-H); 5.13 (dd, $J_{13-H,14-Ha}$)=10.0 Hz, $J_{13-H,14-Hb}$=5.0 Hz, 1H, 13-H); 5.21 (dd, $J_{15-H,14-Ha}$=10.0 Hz, $J_{15-H,14-Hb}$=1.5 Hz, 1H, 15-H); 6.57 (s, 1H, 17-H); 6.94 (s, 1H, TAr—$CH_{arom}$).

$^{13}$C-NMR (100 MHz, $CDCl_3$): δ in ppm=13.4 (16-$CH_3$); 15.7 (6-$CH_3$); 18.0 (8-$CH_3$); 19.0 (TAr—$CH_3$); 22.9 (4-$CH_3$'s); 25.4 (C-11); 31.6+31.7 (C-9 and C-10); 32.5 (C-14); 38.4 (C-8); 39.6 (C-2); 41.7 (C-6); 53.5 (C-4); 72.3 (C-3); 74.1 (C-7); 78.9 (C-15); 115.6 (C-19); 119.2 (C-17); 120.9 (C-13); 138.4 (C-12); 139.2 (C-16); 152.0 (C-18); 165.0 (C-20); 170.4 (C-1); 220.7 (C-5).

$C_{39}H_{69}NO_5SS_2$: (M=720.21 g.$mol^{-1}$)

Example AC

Epothilone B

In 3.5 ml of absolute $CHCl_3$ (put on a column on alox B and distilled of $CaH_2$), 43 mg (87.4 μmol) of the compound that is produced according to Example AB is mixed at −18° C. with 32.5 mg (≈1.5 equivalents, 131.1 μmol, about 70%) of mCPBA and stirred for 5 hours at a temperature that is kept constant.

For working-up, it is diluted with 14 ml of $CH_2Cl_2$, and the reaction is quenched by adding 15 ml of saturated NaHCO$_3$ solution. The phases are separated, the aqueous phase is extracted four more times with CH$_2$Cl$_2$, the combined organic phases are then dried on MgSO$_4$, filtered and concentrated by evaporation.

Chromatographic precleaning on a 1:1-hex/EE-silica gel column produced 36 mg (81.1%) of the title compound as a 4:1 mixture of epothilone B and its α-epoxidisomer. HPLC separation of a small amount was performed on 20% iPrOH in hexane.

$^1$H-NMR (400 MHz, CDCl$_3$): δ in ppm=0.99 (d, J=7.0 Hz, 3H, 8-CH$_3$); 1.07 (s, 3H, 4-CH$_3$); 1.16 (d, J=7.0 Hz, 3H, 6-CH$_3$); 1.27 (s, 3H, 4-CH$_3$); 1.36 (s, 3H, 12-CH$_3$); 1.35–1.45 (m, 3H); 1.46–1.54 (m, 2H); 1.65–1.77 (m, 3H); 1.91 (dd, J=15.6 Hz, J=8.0 Hz, 1H, 14-H); 2.08 (s, 3H, 16-CH$_3$); 2.06–2.13 (m(v), 1H, 14-H); 2.35 (dd, J=13.5 Hz, J=2.5 Hz, 1H, 2-H); 2.53 (dd, J=14.1 Hz, J=10.0 Hz, 1H, 2-H); 2.65 (br, 1H, OH); 2.69 (s, 3H, TAr—CH$_3$); 2.80 (dd, J=7.5 Hz, J=4.5 Hz, 1H, 13-H); 3.29 (qd, J=7.0 Hz, J=4.0 Hz, 1H, 6-H); 3.71 (t, J=4.0 Hz, 1H, 7-H); 4.22 (br, 2H, 3-H and OH); 5.41 (d, J=8.0 Hz, J=3.0 Hz, 1H, 15-H); 6.58 (s, 1H, 17-H); 6.96 (s, 1H, TAr—CH$_{arom}$).

Preparative Methods

All reactions of organometallic reagents and all reactions in absolute solvents are performed in an air-free and moisture-free environment. Before the beginning of the test, the glass devices that are used are heated several times in a vacuum (about 0.01 mbar) and aerated with dried argon of the Linde Company. Unless otherwise indicated, all reaction batches are stirred magnetically.

Methylene chloride is predried on a basic aluminum oxide column of the activity stage I (Woelm) and made absolute on calcium hydride. After predrying on a basic aluminum oxide column over an 8:1 sodium/potassium alloy, diethyl ether is refluxed until stable blue coloring of the benzophenone indicator is achieved and is freshly distilled off before use. Tetrahydrofuran (THF) is predried on KOH, filtered over a column that is coated with basic aluminum oxide and then distilled on potassium with triphenylmethane as an indicator.

After predrying on calcium chloride just like hexane (hex), ethyl acetate (EE) is distilled off in a rotary evaporator before use for column chromatography.

Chromatographic Process

All reactions are tracked by thin-layer chromatography (TLC) on silica gel-60-aluminum foils with UV-indicator F$_{254}$ of the Merck Company. As mobile solvent, in most cases solvent mixtures that consist of hexane (hex) and ethyl acetate (EE) are used. For visualization of non-UV-active substances, anisaldehyde/glacial acetic acid/sulfuric acid (1:100:1) has been taken as a standard immersion reagent in most cases.

The preoperative column chromatography is performed on silica gel-60 of the Merck Company (0.04–0.063 mm, 230–400 mesh), whereby as eluant, solvent mixtures that consist of hexane (hex) and ethyl acetate (EE) or diisopropyl ether are used.

On an analytical scale as well as on a preoperative scale, the high-pressure liquid chromatographic separations (HPLC) are performed on the modular systems of the Knauer Company (pump 64, UV and RI detectors, columns and recorders), Waters/Millipore (injection system U6K9) and Milton-Roy (integrator CI-10). For the analytical HPLC, in most cases a Knauer column (4·250 mm) with 5 μm of Nucleosil is used, and for the preoperative HPLC, a column (16·250 mm, 32·250 mm or 64·300 mm) with 7 μm or 5 μm Nucleosil 50 is used.

Dye Reagents

Dye reagent I (F I): In the case of most compounds that can be reduced, 1 g of cerium(IV) sulfate in 10 ml of concentrated sulfuric acid and 90 ml of water produce an intense blue color reaction during drying.

Dye reagent II (F II): A 10% ethanolic solution of molybdatophosphoric acid produces another immersion reagent for detecting unsaturated compounds that can be reduced. In contrast to dye reagent I, the molybdate dye reagent, especially pertaining to several functionalities, shows a broader color spectrum with virtually identical reliability.

Dye reagent III (F III): 1 ml of anisaldehyde in 100 ml of ethanol and 2 ml of concentrated sulfuric acid produces an extremely sensitive dye reagent that also likely shows the broadest color spectrum.

Dye reagent IV (F IV): Like the anisaldehyde reagent, 1 g of vanillin in 100 ethanol and 2 ml of concentrated sulfuric acid is a very sensitive dye reagent with a broad color spectrum.

Dye reagent V (F V): 1 g of 2,4-dinitrophenylhydrazine in 25 ml of ethanol, 8 ml of water and 5 ml of concentrated sulfuric acid is an excellent immersion reagent that is selective even without heating on aldehyde and that responds somewhat more slowly to ketones.

Dye reagent VI (F VI): A 0.5% aqueous solution of potassium permanganate indicates oxidizable groups by decoloration, whereby unsaturated, non-aromatic structural units react spontaneously without heating.

Spectroscopic Process and General Analysis

NMR Spectroscopy

The $^1$H-NMR spectra are recorded with a DRX 250 DRX 400 spectrometer of the Bruker Company with the substances as a solution in deuterated solvents and tetramethylsilane as an internal standard. The evaluation of the spectra is carried out according to rules of the first order. If a signal multiplicity that occurs cannot be explained in this way, the indication of the observed line assembly is done. To determine the stereochemistry, the NOE-spectroscopy (Nuclear Overhauser Effect) is used.

To characterize the signals, the following abbreviations are used: s (singlet), d (doublet), dd (double doublet), ddd (6-line system with two identical coupling constants or an 8-line system with three different coupling constants), t (triplet), q (quartet), quint (quintet), sext (sextet), sept (septet), m (multiplet), mc (centered multiplet), br (broad), hv (semi-masked signal) and v (masked signal).

The $^{13}$C-NMR spectra are measured with an AC 250 of the Bruker Company with CDCl$_3$-signal at 77.0 ppm as an internal standard, whereby the proton resonances are broadband-decoupled.

IR-Spectroscopy

The infrared spectra are recorded with devices of the Perkin-Elmer Company (Model 257 or 580 B) and Nicolet Company (FTIR Interferometer System 55XC). The oils are measured as films between potassium bromide disks. The bands are indicated according to decreasing wave number (cm$^{-1}$). For characterization, the following designations are selected: vs (very strong), s (strong), m (medium), and w (weak).

Abbreviations abs.: absolute, Ar: aryl/aromatic compound, ber.: calculated, brine: cold, saturated common salt solution, nBuLi: nbutyllithium, c: concentration, COSY: correlated spectroscopy, CSA: camphorsulfonic acid, DC: thin-layer chromatography, DCM: dichloromethane; DDQ: dichlorodicyano-quinone, d.e.: diastereomeric excess, DIBAH: diisobutyl-aluminum hydride, DIPA: diisopropylamine, DMAP: dimethylaminopyridine, DMF: N,N'-dimethylformamide, DMS: dimethyl sulfide, DMSO: dimethyl sulfoxide, ds: diastereoselection, EA: elementary analysis, e.e.: enantiomeric excess, EE: ethyl acetate, EI: electron impact ionization, eq: equivalent(s), eV: electron volt, FG: functional group, FI: field ionization, gef.: found, ges.: saturated, h: hour(s), Hex: n-hexane, HMDS: hexamethyldisilazide, HPLC: high-pressure liquid chromatography, Hunig base: N-ethyl-diisopropylamine, HRMS: high resolution mass spectrometry, HV: high vacuum, iPrOH: 2-propanol, IR: infrared spectrometry/infrared spectrum, J: coupling constant, LDA: lithium diisopropylamine, Lsg.: solution, Lsm.: solvent, MC: methylene chloride, Me: methyl, MeLi: methyllithium, min: minute(s), MS: mass spectrometry/mass spectra, NMR: Nuclear Magnetic Resonance, NOE: Nuclear Overhauser Effect, PCC: pyridinium chlorochromate, PG: protective group, Ph: phenyl, ppm: parts per million, Rkt.: reaction, rt: retention time, RT: room temperature (20–30° C.), Std.: hour(s), TBAF: tetra-n-butylammonium fluoride, TBDPS: tert-butyldiphenyl-silyl-, TBDPSCl: tert-butyldiphenyl-silyl chloride, TBS: tert-butyldimethyl-silyl-, TBSCl: tert-butyldimethyl-silyl chloride, TSBTriflat: tert-butyldimethyl-silyl-triflate, TEA: triethylamine, tert./t: tertiary, TFA: trifluoroethanoic acid.

What is claimed is:

1. A process for production of a compound of formula I:

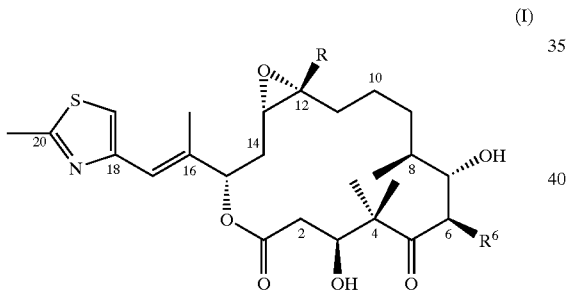

(I)

wherein

R is methyl, and

R$^6$ is a straight-chain or branched-chain alkyl group with up to 6 carbon atoms, a cycloalkylalkyl group with up to 10 carbon atoms, a phenyl group, 1- or 2-naphthyl group, a heteroaryl group, benzyl, or a methylheteroaryl group, said process comprising:

a) reacting a compound of formula 3

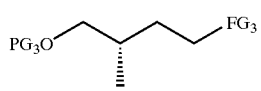

(3)

wherein
PG$_3$ is a hydroxy protective group, and
FG$_3$ is a phenylsulfonyl group, with a compound of formula 4

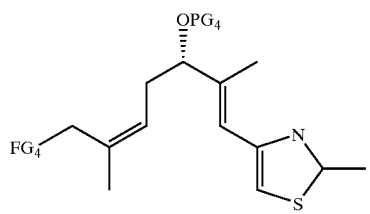

4 wherein

FG$_4$ is an iodine atom or another leaving group, and

PG$_4$ is a hydroxy protective group, to form a compound of formula 34-I

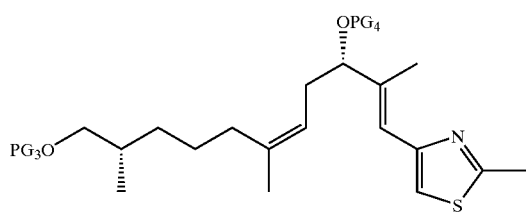

(34-I)

b) reacting the compound of formula 34-I with a compound of formula 2

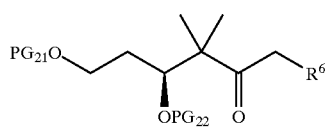

2 wherein

PG$_{21}$ and PG$_{22}$, independently of one another, are in each case a hydroxy protective group, to form a compound of formula 234

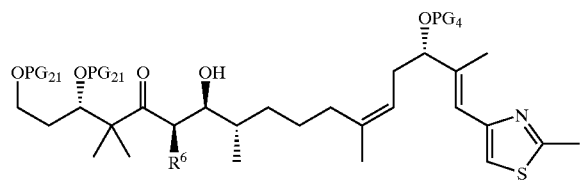

(234)

c) reacting the compound of formula 234 over the following stages

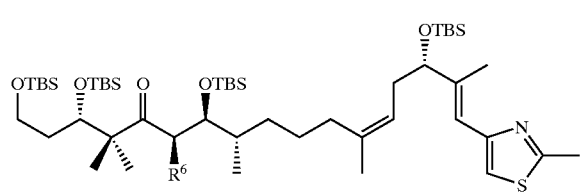

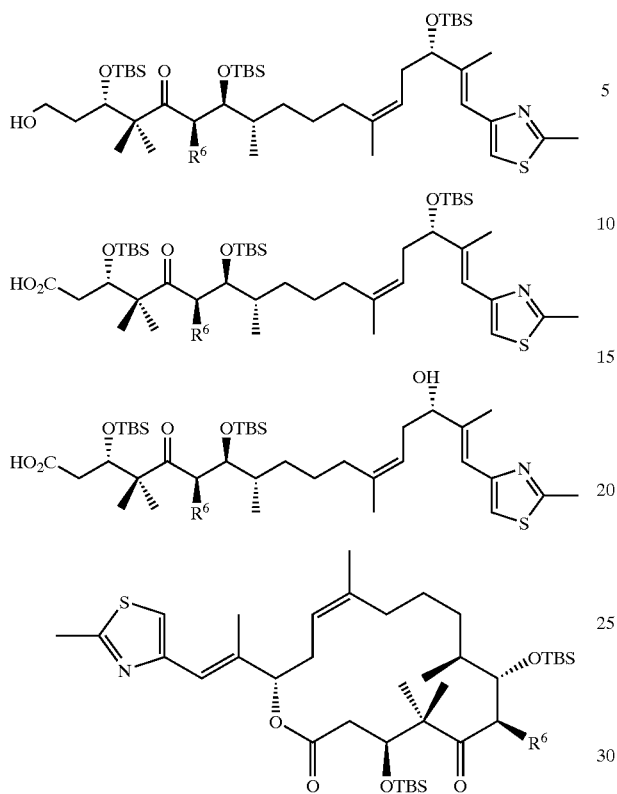

d) converting the resultant compound by epoxidation to form a compound according to formula I.

2. A process according to claim 1, further comprising preparing a compound of formula 2 by (i) reacting a compound of formula 2-I

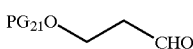 (2-I)

under chiral catalysis with a silylketenacetal of the formula

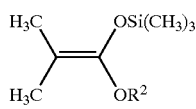

wherein $R^2$ is methyl or ethyl, with mediation by N-tosylvaline/diborane to form a compound of formula 2-II

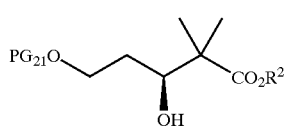 (2-II)

(ii) protecting the 3-hydroxy group of the compound of formula 2-II to obtain a compound of formula 2-III

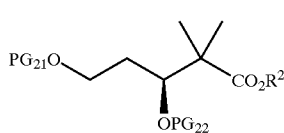 (2-III)

(iii)(a) adding a methyl group to the carbonyl group of the compound of formula 2-III to obtain a compound of formula 2-IV

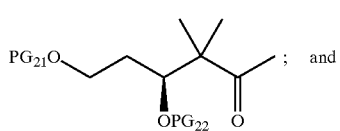 (2-IV)

then converting the compound of formula 2-IV with an alkyl, cycloalkylalkyl, aryl, heteroaryl, methyl, aryl or methylheteroaryl halide of formula 2-X $R^6$Hal (2-X)

wherein

Hal is a halogen atom fluorine, chlorine or bromine, into a compound of formula 2; or (b) reducing the compound of formula 2-III to form an alcohol, selectively oxidizing the alcohol to form an aldehyde, adding a radical of formula —$CH_2$—$R^6$ with an organometallic compound, and oxidizing the alcohol produced to form a ketone of formula 2.

3. A process according to claim 1, further comprising preparing a compound according to formula 3 by converting the free hydroxyl group of the compound of formula 3-I

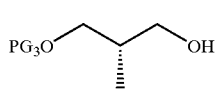 (3-I)

into a leaving group $FG_{31}$, to form a compound of formula 3-II

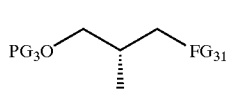 (3-II)

displacing the group $FG_{31}$, and
adding the group —$CH_2$—$SO_2$-phenyl to obtain a compound of formula 3.

4. A process according to claim 1, wherein $PG_{21}$, $PG_{22}$, $PG_3$, and $PG_4$ are each independently alkyl, silyl or acyl radicals.

5. A process according to claim 4, wherein $PG_{21}$, $PG_{22}$, $PG_3$, and $PG_4$ are each independently methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triisopropylsilyl, benzyl, para-nitrobenzyl, para-methoxybenzyl, alkylsulfonyl, arylsulfonyl, unsubstituted formyl, formyl substituted by amino and/or hydroxy groups, unsubstituted acetyl, acetyl substituted with amino and/or hydroxy groups, unsubstituted propionyl, propionyl substituted with amino and/or hydroxy groups, unsubstituted isopropionyl, isopropionyl substituted with amino and/or hydroxy, unsubstituted pivalyl, pivalyl substituted with amino and/or hydroxy, groups, un substituted butyryl, butyryl substituted with amino and/or hydroxy group, unsubstituted benzoyl, or benzoyl substituted with amino and/or hydroxy groups.

6. A process according to claim 4, wherein $PG_{21}$, $PG_{22}$, $PG_3$, and $PG_4$ are each independently trimethylsilyl, tert-butyldimethylsilyl, triisopropylsilyl, triethylsilyl, or tert-butyldiphenylsilyl.

7. A process according to claim 4, wherein $PG_{21}$, $PG_{22}$, $PG_3$, and $PG_4$ are each independently tert-butyldimethylsilyl, triisopropylsilyl, or tert-butyldiphenylsilyl.

8. A process according to claim 1, wherein $R^6$ is methyl, ethyl, propyl, isopropyl, butyl, isobutyl, tert-butyl, pentyl, isopentyl, neopentyl, or hexyl, which in each case is unsubstituted or substituted one or more times by halogen, OH, O-alkyl, $CO_2H$, $CO_2$-alkyl, $-NH_2$, $-NO_2$, $-N_3$, $-CN$, $C_1-C_{20}$ alkyl, $C_1-C_{20}$ acyl, or $C_1-C_{20}$ acyloxy.

9. A process according to claim 1, wherein $R^6$ is cyclopropylmethyl, cyclobutylmethyl, cyclopentylmethyl or cyclohexylmethyl, which in each case is unsubstituted or substituted one or more times by halogen, OH, O-alkyl, $CO_2H$, $CO_2$-alkyl, $-NH_2$, $-NO_2$, $-N_3$, $-CN$, $C_1-C_{20}$ alkyl, $C_1-C_{20}$ acyl, or $C_1-C_{20}$ acyloxy.

10. A process according to claim 1, wherein $R^6$ is a furyl, thienyl, pyridyl, pyrazolyl, pyrimidinyl, oxazolyl, pyridazinyl, pyrazinyl, quinolyl, or thiazolyl, or is a methylheteroaryl group in which the heteroaryl group is a furyl, thienyl, pyridyl, pyrazolyl, pyrimidinyl, oxazolyl, pyridazinyl, pyrazinyl, quinolyl, or thiazolyl, wherein in each case the heteroaryl group is unsubstituted or substituted one or more times by halogen, OH, O-alkyl, $CO_2H$, $CO_2$-alkyl, $-NH_2$, $-NO_2$, $-N_3$, $-CN$, $C_1-C_{20}$ alkyl, $C_1-C_{20}$ acyl, or $C_1-C_{20}$ acyloxy, and heteroatoms are oxidized or unoxidized.

11. A process according to claim 1, wherein $R^6$ is methyl, ethyl, propyl, isopropyl, butyl, isobutyl, tert-butyl, pentyl, isopentyl, neopentyl, or hexyl, which in each case is unsubstituted or substituted one or more times by halogen, OH, O-alkyl, $CO_2H$, $CO_2$-alkyl, $-NH_2$, $-NO_2$, $-N_3$, $-CN$, $C_1-C_{20}$ alkyl, $C_1-C_{20}$ acyl, or $C_1-C_{20}$ acyloxy;

cyclopropylmethyl, cyclobutylmethyl, cyclopentylmethyl or cyclohexylmethyl, which in each case is unsubstituted or substituted one or more times by halogen, OH, O-alkyl, $CO_2H$, $CO_2$-alkyl, $-NH_2$, $-NO_2$, $-N_3$, $-CN$, $C_{1-C20}$ alkyl, $C_1-C_{20}$ acyl, or $C_1-C_{20}$ acyloxy; or furyl, thienyl, pyridyl, pyrazolyl, pyrimidinyl, oxazolyl, pyridazinyl, pyrazinyl, quinolyl, or thiazolyl, or is a methylheteroaryl group in which the heteroaryl group is a furyl, thienyl, pyridyl, pyrazolyl, pyrimidinyl, oxazolyl, pyridazinyl, pyrazinyl, quinolyl, or thiazolyl, wherein in each case the heteroaryl group is unsubstituted or substituted one or more times by halogen, OH, O-alkyl, $CO_2H$, $CO_2$-alkyl, $-NH_2$, $-NO_2$, $-N_3$, $-CN$, $C_1-C_{20}$ alkyl, $C_1-C_{20}$ acyl, or $C_1-C_{20}$ acyloxy, and heteroatoms are oxidized or unoxidized.

12. A process according to claim 5, wherein $R^6$ is methyl, ethyl, propyl, isopropyl, butyl, isobutyl, tert-butyl, pentyl, isopentyl, neopentyl, or hexyl, which in each case is unsubstituted or substituted one or more times by halogen, OH, O-alkyl, $CO_2H$, $CO_2$-alkyl, $-NH_2$, $-NO_2$, $-N_3$, $-CN$, $C_1-C_{20}$ alkyl, $C_1-C_{20}$ acyl, or $C_1-C_{20}$ acyloxy;

cyclopropylmethyl, cyclobutylmethyl, cyclopentylmethyl or cyclohexylmethyl, which in each case is unsubstituted or substituted one or more times by halogen, OH, O-alkyl, $CO_2H$, $CO_2$-alkyl, $-NH_2$, $-NO_2$, $-N_3$, $-CN$, $C_1-C_{20}$ alkyl, $C_1-C_{20}$ acyl, or $C_1-C_{20}$ acyloxy; or furyl, thienyl, pyridyl, pyrazolyl, pyrimidinyl, oxazolyl, pyridazinyl, pyrazinyl, quinolyl, or thiazolyl, or is a methylheteroaryl group in which the heteroaryl group is a furyl, thienyl, pyridyl, pyrazolyl, pyrimidinyl, oxazolyl, pyridazinyl, pyrazinyl, quinolyl, or thiazolyl, wherein in each case the heteroaryl group is unsubstituted or substituted one or more times by halogen, OH, O-alkyl, $CO_2H$, $CO_2$-alkyl, $-NH_2$, $-NO_2$, $-N_3$, $-CN$, $C_1-C_{20}$ alkyl, $C_1-C_{20}$ acyl, or $C_1-C_{20}$ acyloxy, and heteroatoms are oxidized or unoxidized.

13. A process according claim 1, wherein said compound of formula 3 is (3S)-4-[(1,1-Dimethylethyl)dimethylsilyloxy]-3-methyl-1-phenylsulfonyl-butane.

14. A process according claim 1, wherein said compound of formula 4 is (5S,2Z,6E)-2,6-Dimethyl-5-[(1,1-dimethylethyl)-dimethylsilyloxy]-7-(2-methylthiazol-4-yl)hepta-2,6-dienol.

15. A process according claim 1, wherein said compound of formula 34-I is (2S,6Z,9S,10E)-1,9-Bis[(1,1-dimethylethyl)dimethylsilyloxy]-11-(2-methylthiazol-4-yl)-2,6,10-trimethyl-undeca-6,10-diene.

16. A process according claim 1, wherein said compound of formula 2 is (5S)-5,7-Bis[(1,1-dimethylethyl)dimethylsilyloxy]-4,4-dimethyl-heptan-3-one.

17. A process according claim 1, wherein said compound of formula 234 is (3S,6R,7S,8S,12Z,15S,16E)-4,4,6,8,12,16-Hexamethyl-7-hydroxy-16-(2-methylthiazol-4-yl)-1,3,15-tris[(1,1-dimethylethyl)dimethylsilyloxy]-hepta-dec-12,16-dien-5-one.

18. A process comprising:

a) reacting a compound of formula 3

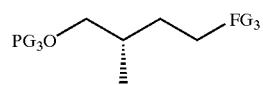

wherein $PG_3$ is a hydroxy protective group, and $FG_3$ is a phenylsulfonyl group, with a compound of formula 4

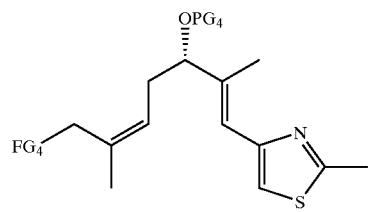

4 wherein $FG_4$ is an iodine atom or another leaving group, and $PG_4$ is a hydroxy protective group, to form a compound of formula 34-I

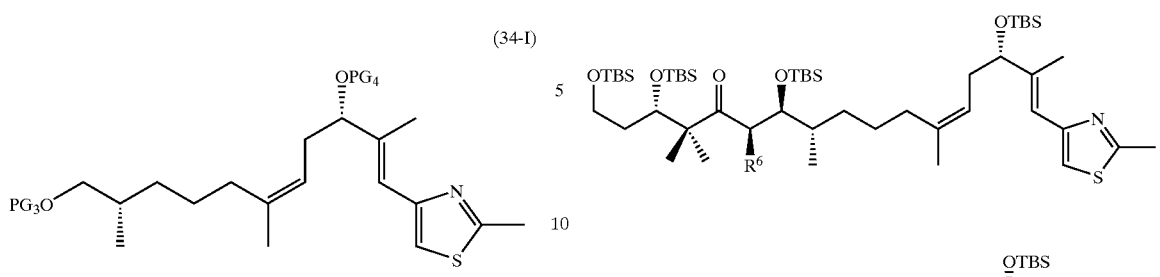

(34-I)

b) reacting the compound of formula 34-I with a compound of formula 2

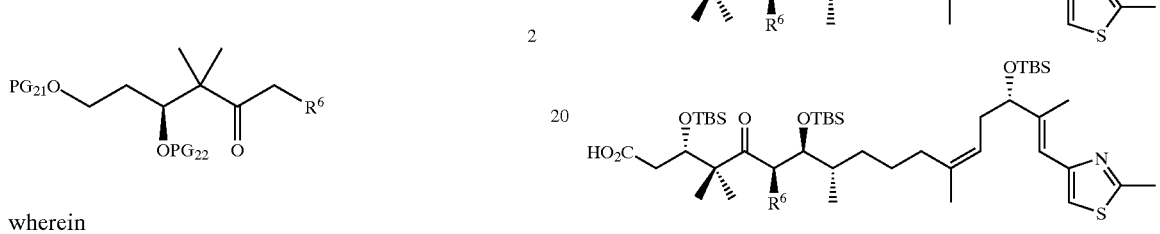

2 wherein
PG$_{21}$ and PG$_{22}$, independently of one another, are in each case a hydroxy protective group, and
R$^6$ is a straight-chain or branched-chain alkyl group with up to 6 carbon atoms, a cycloalkylalkyl group with up to 10 carbon atoms, a phenyl group, 1- or 2-naphthyl group, a heteroaryl group, benzyl, or a methylheteroaryl group, to form a compound of formula 234

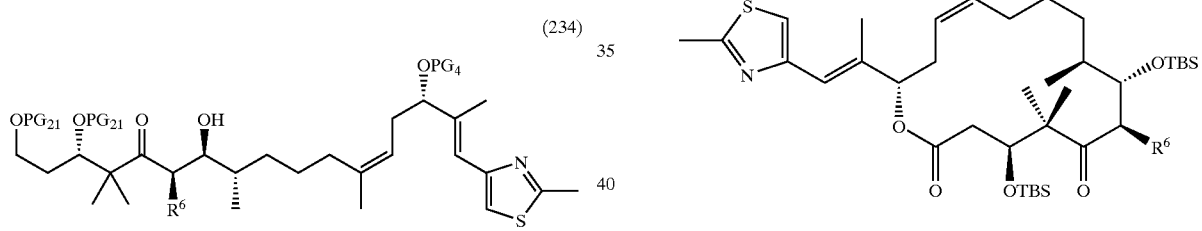

(234)

c) reacting the compound of formula 234 over the following stages

* * * * *